US006577387B2

(12) United States Patent  (10) Patent No.: US 6,577,387 B2
Ross, III et al.  (45) Date of Patent: Jun. 10, 2003

(54) INSPECTION OF OPHTHALMIC LENSES USING ABSORPTION

(75) Inventors: Denwood F. Ross, III, Jacksonville, FL (US); Mary L. Dolan, Jacksonville, FL (US); Ranganath R. Raja, Jacksonville, FL (US); Brian G. Rice, Jacksonville, FL (US); Craig W. Walker, Jacksonville, FL (US); David Kappel, San Diego, CA (US); Robert E. Fischer, Westlake Village, CA (US); Ture Kindt-Larsen, Holte (DK)

(73) Assignee: Johnson & Johnson Vision Care, Inc., Jacksonville, FL (US)

( * ) Notice: Subject to any disclaimer, the term of this patent is extended or adjusted under 35 U.S.C. 154(b) by 152 days.

(21) Appl. No.: 09/751,875

(22) Filed: Dec. 29, 2000

(65) Prior Publication Data

US 2002/0122172 A1 Sep. 5, 2002

(51) Int. Cl.$^7$ .................................................. G01B 9/00
(52) U.S. Cl. ....................................................... 356/124
(58) Field of Search ................................ 356/124–127; 250/461.1

(56) References Cited

U.S. PATENT DOCUMENTS

| | | |
|---|---|---|
| 1,464,999 A | 8/1923 | Pyser |
| 3,072,585 A | 1/1963 | Milonis et al. |
| 3,399,173 A | 8/1968 | Heller et al. |
| 3,841,760 A | 10/1974 | Guyton |
| 3,985,445 A | 10/1976 | Tagnon |
| 4,118,730 A | 10/1978 | Lemelson |
| 4,148,061 A | 4/1979 | Lemelson |
| 4,338,626 A | 7/1982 | Lemelson |
| 4,362,943 A | 12/1982 | Presby |
| 4,408,291 A | 10/1983 | Gunzberg et al. |
| 4,495,313 A | 1/1985 | Larsen |
| 4,511,918 A | 4/1985 | Lemelson |
| 4,528,311 A | 7/1985 | Beard et al. |
| 4,565,348 A | 1/1986 | Larsen |

(List continued on next page.)

FOREIGN PATENT DOCUMENTS

| | | |
|---|---|---|
| CA | 2057832 | 6/1992 |
| DE | 24 31 156 | 12/1975 |
| DE | 34 32 002 A1 | 3/1986 |
| DE | 41 23 554 A1 | 1/1992 |
| EP | 0 063 761 A1 | 11/1982 |
| EP | 0 604 174 B1 | 6/1994 |
| EP | 0 604 174 A3 | 6/1994 |
| EP | 0 604 174 A2 | 6/1994 |
| EP | 0 604 178 B1 | 6/1994 |
| EP | 0 604 178 A1 | 6/1994 |
| EP | 0 604 179 A2 | 6/1994 |
| EP | 0 604 180 A3 | 6/1994 |
| EP | 0 604 180 A2 | 6/1994 |
| EP | 0 605 171 A2 | 7/1994 |
| EP | 0 605 990 A2 | 7/1994 |
| EP | 0 605 990 A3 | 7/1994 |
| EP | 0 607 692 B1 | 7/1994 |
| EP | 0 607 692 A3 | 7/1994 |
| EP | 0 686 585 A2 | 12/1995 |
| EP | 1 050 470 A1 | 11/2000 |
| GB | 2 171 812 A | 9/1986 |
| JP | Sho 63-21533 | 1/1988 |
| WO | WO 00/46582 | 8/2000 |

Primary Examiner—Michael P. Stafira

(57) ABSTRACT

A method and system for inspecting ophthalmic lenses using absorption where an ophthalmic lens is illuminated with light comprising wavelengths that are substantially absorptive to said lens, the image subsequently detected being created using only light at said absorptive wavelengths. Variations in transmitted light intensity translate into thickness changes in the lens caused by cosmetic flaws. The invention is also directed to imaging lens assemblies employing highly positive-powered field flattening lens elements to image a curved object, such as an ophthalmic lens, onto a flat image plane.

47 Claims, 13 Drawing Sheets

U.S. PATENT DOCUMENTS

| | | |
|---|---|---|
| 4,640,489 A | 2/1987 | Larsen |
| 4,680,336 A | 7/1987 | Larsen et al. |
| 4,691,820 A | 9/1987 | Martinez |
| 4,716,234 A | 12/1987 | Dunks et al. |
| 4,719,248 A | 1/1988 | Bambury et al. |
| 4,868,251 A | 9/1989 | Reich et al. |
| 4,889,664 A | 12/1989 | Kindt-Larsen et al. |
| 4,956,783 A | 9/1990 | Teranishi et al. |
| 4,969,038 A | 11/1990 | Lemelson |
| 4,979,029 A | 12/1990 | Lemelson |
| 4,980,993 A | 1/1991 | Umezaki |
| 4,984,073 A | 1/1991 | Lemelson |
| 5,023,714 A | 6/1991 | Lemelson |
| 5,039,459 A | 8/1991 | Kindt-Larsen |
| 5,066,120 A | 11/1991 | Bertrand |
| 5,067,012 A | 11/1991 | Lemelson |
| 5,080,839 A | 1/1992 | Kindt-Larsen |
| 5,089,122 A | 2/1992 | Chmiel |
| 5,094,609 A | 3/1992 | Kindt-Larsen |
| 5,119,190 A | 6/1992 | Lemelson |
| 5,119,205 A | 6/1992 | Lemelson |
| 5,128,753 A | 7/1992 | Lemelson |
| 5,134,574 A | 7/1992 | Beaverstock et al. |
| 5,173,739 A | 12/1992 | Kurachi et al. |
| 5,247,341 A | 9/1993 | Kurachi et al. |
| 5,301,004 A | 4/1994 | Percival et al. |
| 5,303,023 A | 4/1994 | Portney et al. |
| 5,379,111 A | 1/1995 | Kajino et al. |
| 5,399,867 A | 3/1995 | Kohno |
| 5,432,596 A | 7/1995 | Hayashi |
| 5,443,152 A | 8/1995 | Davis |
| 5,461,570 A | 10/1995 | Wang et al. |
| 5,500,732 A | 3/1996 | Ebel et al. |
| 5,574,554 A | 11/1996 | Su et al. |
| 5,604,583 A | 2/1997 | Byron et al. |
| 5,633,504 A | 5/1997 | Collins et al. |
| 5,719,669 A | 2/1998 | Ross, III |
| 5,748,300 A | 5/1998 | Wilder et al. |
| 5,801,822 A | 9/1998 | Lafferty et al. |
| 5,818,573 A | 10/1998 | Lafferty et al. |
| 5,828,446 A | 10/1998 | Davis |
| 5,847,819 A * | 12/1998 | Yanagi ..................... 356/124 |
| 5,882,698 A | 3/1999 | Su et al. |
| 5,929,970 A | 7/1999 | Mihashi |
| 6,018,931 A | 2/2000 | Byram et al. |
| 6,020,445 A | 2/2000 | Vanderlaan et al. |
| 6,024,448 A | 2/2000 | Wu et al. |
| 6,031,059 A | 2/2000 | Vanderlaan et al. |
| 6,042,230 A | 3/2000 | Neadle et al. |
| 6,047,082 A | 4/2000 | Rhody et al. |
| 6,118,528 A * | 9/2000 | Yanagi ..................... 356/246 |
| 6,246,062 B1 * | 6/2001 | Ross et al. ............... 250/461.1 |

\* cited by examiner

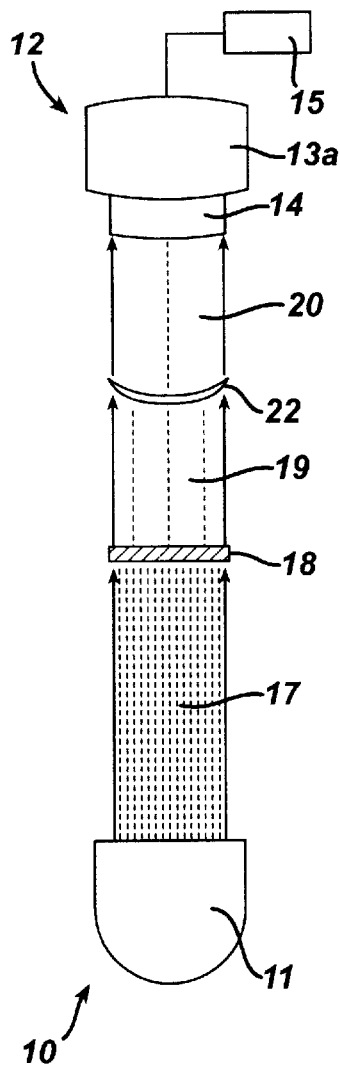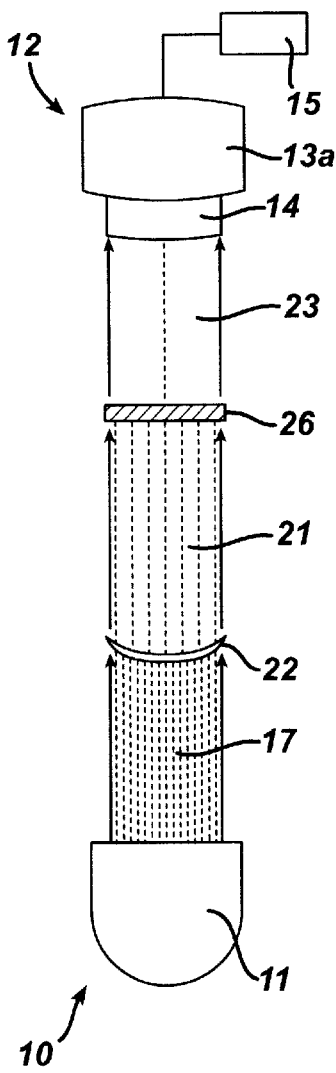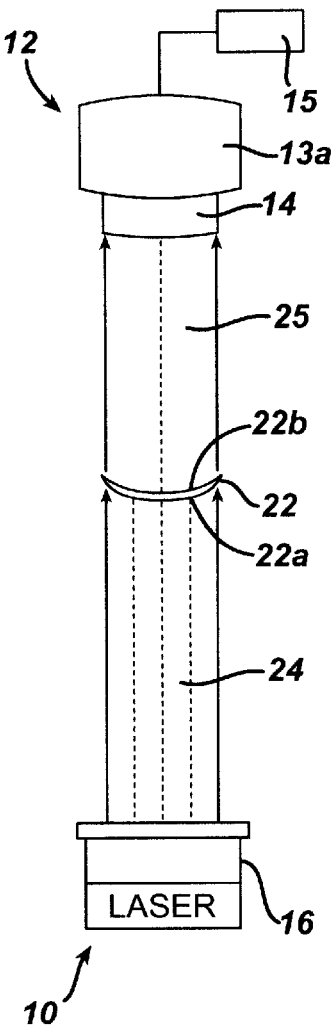

INSPECTION OF OPHTHALMIC LENSES USING ABSORPTION

BACKGROUND OF THE INVENTION:

1. Field of the Invention

The invention pertains to the inspection of optical media, such as ophthalmic lenses. More particularly, it relates to a method and system for inspecting ophthalmic lenses using light at wavelengths that are substantially absorptive to the ophthalmic lens, e.g. light at select ultraviolet (UV) or infrared (IR), wavelengths when the lens is a soft contact lenses. In an image of the lens generated therefrom, thickness changes caused by cosmetic flaws or thickness changes that are deliberately designed into the ophthalmic lens, manifest as measurable changes in transmitted light intensity. In practice, the invention reduces the number of false rejections by enabling a significant increase in the level of discrimination between cosmetic flaws critical to lens quality and extraneous artifacts which are not; and permits verification that intentional changes in lens thickness meet specification. The invention is especially adaptable to high speed, automated inspection. In certain embodiments involving soft contact lenses, the invention can be implemented without removing the lenses from the molds in which they are made, thus creating greater efficiencies in the inspection process.

2. Description of the Prior Art

Various techniques for inspecting ophthalmic lenses exist. Initial endeavors relied upon human inspectors to visually examine the lens for defects. These usually-entailed placing the lens under magnification or projecting it onto a screen whereafter the inspector would manually search for irregularities by e.g. varying the field of focus to examine the lens for flaws at different depths. The labor intensive and subjective nature of human operator inspections impelled interest in automating aspects of the process. For example, methods have been developed whereby an image of the lens is generated and electronically evaluated for defects. These commonly take advantage of the fact that light, under certain conditions, scatters in a manner that can be qualitatively assessed when it encounters a lens irregularity. These methods ordinarily employ white light because of its convenient availability, and because they do not require light of a specific spectral profile for functionality. Indeed, such methods avail themselves of the fact that the ophthalmic lens is effectively transparent to the inspection light, and operate by manipulating the light beam before and/or after it passes through the lens to extract the necessary optical information that is subsequently analyzed to assess for flaws.

The more common of such lens inspection methods involve imaging the lens under either dark field (DF) illumination or bright field (BF) illumination conditions. In dark field, the manipulation of the light beam entails partially blocking the light source so that only light rays whose path through the ophthalmic lens have been disrupted (e.g. by a lens flaw or irregularity) will be imaged. In a dark field system, anything that causes a change in the optical path of light rays traversing the lens will be greatly enhanced and will appear in the image as a bright spot on a dark field. An example of a dark field illumination lens inspection technique is described in Canadian Patent Application 2057832. In bright field, the ophthalmic lens is typically fully illuminated by the light source, i.e. the light source is not partially blocked. Such a technique is described in U.S. Pat. No. 5,500,732, which illuminates the lens at specified grey levels to which the imaging camera is sensitive; irregularities in the ophthalmic lens then appear in the image as dark spots against a bright field.

While some of these techniques have proven industrially useful, there nevertheless exists an impetus to continually improve contrast in the lens image to further distinguish defective from non-defective areas of the lens, as well as discrimination between cosmetic flaws that are fatal to lens quality and extraneous lens artifacts that are not. Because white light is employed in these prior techniques, irrelevant lens detail is often imaged while important detail is lost. This can result in too many false rejections of lenses. Investigations into other types of lens inspection techniques include that which is reported in: U.S. Pat. No. 5,633,504 wherein the lens is imaged under conditions of fluorescence. Such a method is limited, however, by the types of materials that can be analyzed by fluorescence.

Furthermore, these earlier techniques are inadequate to measure deliberate changes in lens thickness, such as occurs with toric thin zones in certain types of contact lenses, to verify that they meet specification. These toric thin zones are intentionally provided and allow for rotational positioning on the lens on the eyeball.

Moreover, the practices of the prior art require improvements in the lenses employed in the imaging apparatus. Conventionally, the imaging lenses utilized in imaging devices known heretofore have had flat focal surfaces. Representative of art in this regard is U.S. Pat. No. 5574554 which uses a combination of collimated white light and a telecentric imaging lens. The difficulty with such configurations, however, is that the ophthalmic lens being imaged is oftentimes curved (e.g. to fit the eyeball in the case of a contact lens),not flat. In particular, the art typically utilizes a negatively powered lens element having a small beam diameter in front of the flat imaging plane in the imaging device. The result is a compromise in focus, to the diminishment of the inspection process.

Hence the ophthalmic lens inspection art continually seeks to explore and develop techniques that will heighten discernible contrasts between fatal cosmetic flaws and non-fatal extraneous artifacts, which techniques will lead to a decrease in the number of false rejections and be easily implemented leading to inspection efficiencies.

SUMMARY OF THE INVENTION

The present invention is directed to the inspection of ophthalmic lenses utilizing an absorptive technique. In one aspect, the invention is directed to a method for inspecting ophthalmic lenses which comprises illuminating an ophthalmic lens with light comprising a wavelength that is substantially absorptive to said ophthalmic lens; detecting an image of at least part of said ophthalmic lens only from light that is at said substantially absorptive wavelength which has been transmitted through said lens; and analyzing said image for changes in the intensity of the light that is at said absorptive wavelength which has been transmitted through said lens. In the practice of the invention, the changes in transmitted light intensity as aforesaid are caused by changes in thickness of the ophthalmic lens. These can be caused by cosmetic flaws, irregularities or can be due to the design of a particular ophthalmic lens. The present invention also pertains to a system for such inspections. In another aspect especially useful where the ophthalmic lens has curvature (e.g. a contact lens), the invention relates to an imaging lens assembly for an imaging sensor, the imaging lens assembly having a curved focal surface to match the curvature of the ophthalmic lens, thus ameliorating focus and consequent image analysis. The invention is further directed to a lens assembly that directs inspection light onto the surface of the ophthalmic lens at angles of incidence that are substantially normal to said surface. The invention is also directed to a lens carrier having a specific frustroconical well design; and to a specific apodizer.

BRIEF DESCRIPTION OF THE DRAWINGS

FIGS. 1A, 1B and 1C are block diagrams showing the layout for three embodiments of the inspection technique of the invention.

DETAILED DESCRIPTION OF THE INVENTION

Figure 2:
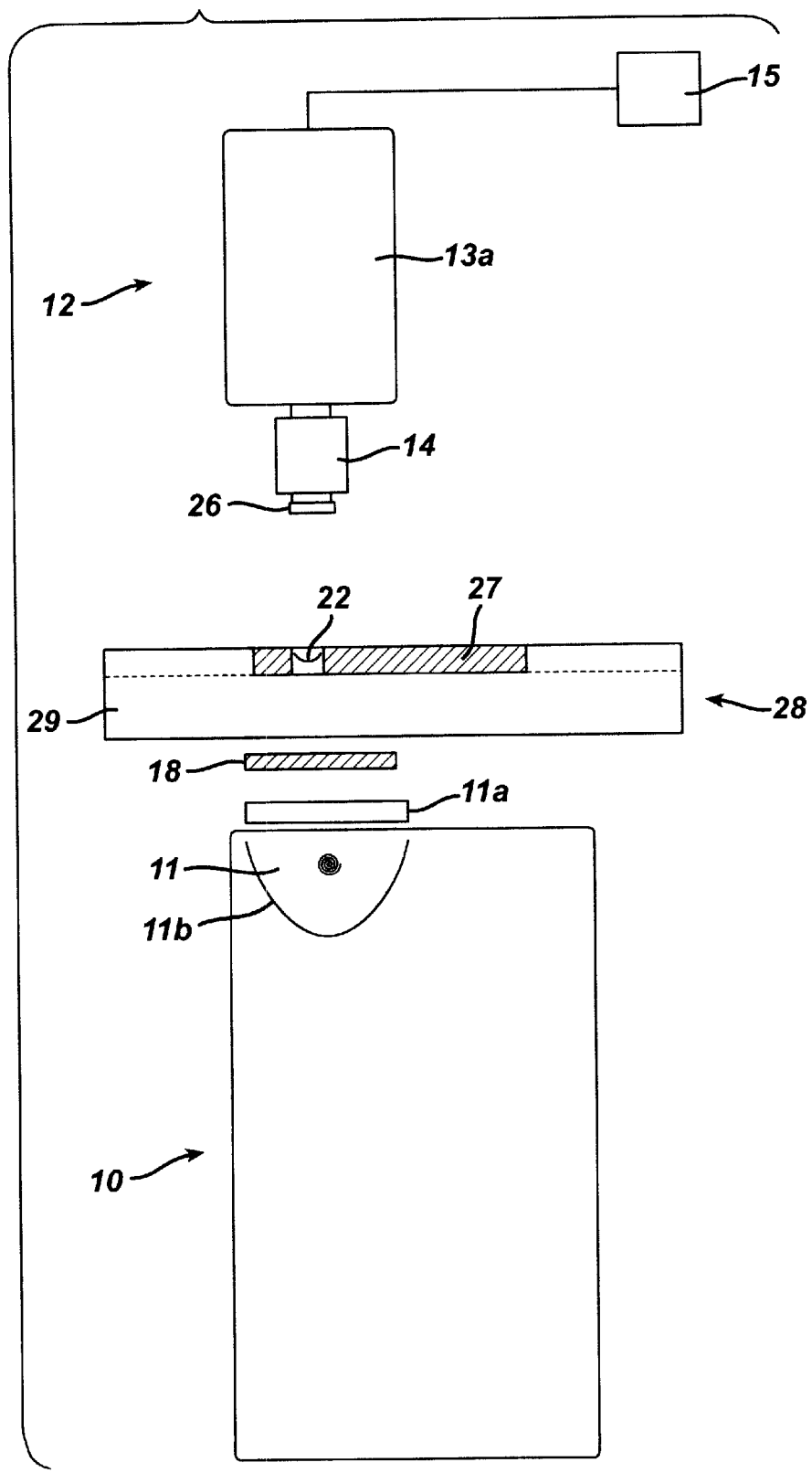
FIG. 2 is a detail of the layouts shown in FIGS. 1A and 1B.

The present invention pertains to the inspection of ophthalmic lenses for cosmetic flaws. Examples of ophthalmic lenses in this regard include hard, soft, rigid gas permeable contact and intraocular lenses, and lenses for eyeglasses. The invention has especial utility for soft contact lenses commonly classified as hydrogel lenses; these are generally prepared from monomers including but not limited to hydroxyethyl methacrylate (HEMA), vinyl pyrrolidone, glycerol methacrylate, methacrylic acid and acid esters. While not constraining the present invention, soft lenses in this regard are typically prepared by free radical polymerization of monomer mix in a plastic mold having male and female halves of predetermined shape and characteristic. The monomer mix may contain other additives as known in the art, e.g. crosslinking and strengthening agents. Polymerization is conventionally initiated by thermal means, or is photoinitiated using either UV or visible light. In these cases, the plastic molds in which polymerization occurs are effectively transparent to the photoinitiating light. Plastics that commonly serve as materials of construction for plastic molds in this regard include without limitation: polyolefins, such as low-, medium-, and high-density polyethylene, polypropylene, and copolymers thereof; polystyrene; poly4-methylpentene; polyacetal resins; polyacrylether; polyarylether, sulfones; Nylon 6; Nylon 66; Nylon 11; thermoplastic polyester and various fluorinated materials such as the fluorinated ethylene propylene copolymers and ethylene fluoroethylene copolymers. After polymerization, the lenses are inspected, with those having cosmetic flaws rejected.

In the present invention, it is only light at a wavelength that is substantially absorptive to a particular ophthalmic lens that is detected and used to create the image of the ophthalmic lens; to the extent such light has been transmitted by said lens. This includes whatever light that has been able to penetrate through the lens material itself, and includes light that has not passed through the opthalmic lens material itself, but rather has traversed the opthalmic lens by traveling through e.g. a hole or tear in the lens, which constitute types of cosmetic flaws identifiable by the invention..

In the present specification, the terms "wavelength substantially absorptive," "wavelength that is substantially absorptive," "substantially absorptive wavelength" and the like are used interchangeably. As used herein, these terms refer to light having a spectral profile that is substantially absorbed by the ophthalmic lens because of its material of construction (e.g. HEMA) and/or by additives included in the lens for this purpose. This means that very little, if any, of this light is transmitted through the ophthalmic lens, and that changes in ophthalmic lens thickness caused e.g. by holes, tears, chips; or by deliberate design, e.g. toric thin zones, create measurable changes in the intensity of transmitted light. As a quantitative matter, light is absorbed (or conversely, transmitted) by an ophthalmic lens in accordance with Beer's Law, which states that the intensity of transmitted light decreases exponentially with an increase in path length. In the context of the invention, this means that an increase in the path length of inspection light through the ophthalmic lens will result in an exponential diminishment in the intensity of the transmitted light that can be imaged and subsequently analyzed. Hence, in the practice of the invention, light at a substantially absorptive wavelength is light whose the spectral profile is such that the intensity of light transmitted through the thinnest part of the ophthalmic lens does not saturate the image of that part created on the image sensor. Preferably, the spectral profile is chosen such that the intensity of light transmitted through the thickest part of the ophthalmic lens is just above zero (i.e. just enough to register an image) and the intensity of the light transmitted through the thinnest part of the lens is just under the point of image saturation. While the percentage of light absorbed (or conversely, light transmitted) by an ophthalmic lens can vary within the spirit and scope of the invention, it is preferred that light at a substantially absorptive wavelength is light having a spectral profile such that at least 75% of said light is absorbed by the ophthalmic lens at its thickest part; more preferably, at least 85%; still more preferably at least 90%; and yet still more preferably at least 95% is absorbed by said lens at its thickest part (conversely, no more than 25%, more preferably no more than 15%, still more preferably no more than 10% and yet still more preferably no more than 5% of such light is transmitted through the lens at its thickest part, respectively). In the practice of the invention, such light can be constituted of one or more wavebands or one or more single wavelengths within the region that is substantially absorbed by the lens. As an example, for soft contact lenses comprising HEMA, only about 5% of incident light having a wavelength of up to about 400 nm will penetrate the center of a 70 um thick HEMA-based soft contact lens because of the added UV blocker, e.g. NORBLOCK. In the practice of the invention, however, an abrupt variation in contact lens thickness, e.g. a variation having a magnitude typically associated with a cosmetic flaw, will cause a measurable variation in the intensity of light transmitted through the HEMA lens (comprising the UV blocker) at that point. Hence, where there has been removal of lens material, such as with a hole, there is greater transmission of light; where there has been addition of material, such as caused by debris, there is greater absorption of light. The invention is also non-fluorescent, and is thus not limited in choice of materials that fluoresce inasmuch as it is preferred that the absorbed wavelength(s) and the detected wavelength(s) are the same.

In practice, the present invention provides for more robust inspection for cosmetic flaws. That is, the invention permits one to distinguish cosmetic flaws that are important to lens quality, against other artifacts that are less so, by enhancing the contrast between the two. Cosmetic flaws that are important to lens quality, such as chips, tears, voids, and marks, typically manifest as relatively abrupt changes in the thickness of the lens; the consequent detection of these is enhanced by the absorptive technique of the invention. On the other hand, the less important extraneous defects, such as pulls, scuff marks and water marks, typically do not manifest as abrupt changes in lens thickness; accordingly, these are not enhanced and are effectively suppressed in the practice of the invention. By facilitating such discrimination, the invention enables a more exacting inspection to occur, the result being tighter quality control with fewer false rejections.

The present invention comprises a method and system for inspecting an ophthalmic lens which comprises (a) illuminating an ophthalmic lens with light at a wavelength substantially absorptive to said lens; (b) detecting an image of at least part of said ophthalmic lens only from light that is at said wavelength and that has been transmitted through said ophthalmic lens; and (c) analyzing said image for changes in intensity of the light that is at said wavelength and that has been transmitted through said ophthalmic lens, said changes in intensity caused by changes in thickness of said ophthalmic lens that are due to cosmetic flaws; or that are caused by changes in thickness that are deliberately designed into the lens.

In regard to illumination step (a):

Without limitation, the following practices are preferred for illumination step (a). In the first practice, the ophthalmic lens is illuminated with light that is already at the absorptive wavelength. In one embodiment of this first practice light from a conventional light source, such as a non-laser light source, e.g. a xenon flash lamp, is filtered to provide the absorptive wavelength with which the ophthalmic lens is illuminated. For example, a bandpass filter adequate to block out all but the absorptive wavelength can be interposed between the light source and the ophthalmic lens. In another embodiment of this first practice, the light source itself generates the absorptive wavelength in the first instance, without need for filtering out specific wavelengths. For example, a laser configured to emit light at the absorptive wavelength can be employed to illuminate the ophthalmic lens.

In another practice of step (a), the ophthalmic lens is illuminated with light that contains the absorptive wavelength, but also contains a significant quantity of wavelengths that are transmitted as well, such as light obtained from a conventional light source, e.g. a xenon flash lamp. In this practice of the invention, the light that has been transmitted through the ophthalmic lens is filtered after the fact, i.e. after it has passed through the ophthalmic lens, using an appropriate bandpass filter, but prior to the image detection of step (b). Hence, consistent with the principles of the invention irrespective of which embodiment is employed, only light that is at the absorptive wavelength is used to detect and create the image of the lens that is subsequently analyzed for cosmetic flaws.

The absorptive wavelength employed in the invention depends on the material of construction used for the ophthalmic lens, as well as the optional presence of absorption additives deliberately added to the lens, e.g. into the monomer mix in the case of a soft contact lens, to manipulate the absorption properties of the final ophthalmic lens product subject of inspection.

In a preferred embodiment of the invention, the ophthalmic lens is comprised of HEMA, e.g. as used to manufacture a soft hydrogel contact lens. For soft contact lenses in particular, one or more ultraviolet absorption additives can be included in the monomer mix for the lens, the resultant ophthalmic lens being substantially opaque to wavelengths up to about 400 nm. Absorbers of this kind include NORBLOCK (commercially available from Janssen). While the amount of such additives can vary, and depends upon the final absorption behavior being'sought, it is typical that such additives are present in an amount of approximately 1 part absorber per hundred parts HEMA. Other absorptive materials in a contact lens would include tints which would be useful in an inspection process which images the contact lens based on the absorption of particular wavelengths, e.g. yellow light, which would be absorbed by a contact lens having a blue tint. Alternatively, the amount of water in the lens could be used to absorb an infrared light, and the portion of infrared light that was. transmitted through the lens could be used to image the lens.

In a preferred embodiment of the invention, the absorptive wavelength for light used for illumination is up to about 400 nm; more typically from about 200 nm to about 400 nm; more preferably between about 280 nm to about 360 nm; still more preferably between about 320 nm to about 355 nm. In practice, these wavelengths are especially useful for, but not limited to, soft contact lenses comprising HEMA and a UV absorptive material. However, for light in the visible range the incident light Would preferably comprise about 400 nm to about 700 nm more preferably from about 560 nm to about 640 nm. In another embodiment of the invention the absorptive wavelengths are generally in the infrared, including wavelengths at least about 700 nm, e.g. about 700 nm to about 1000 nm.

While various preferred absorptive wavelengths are described herein as being in the UV and IR regions, the practice of the invention is not limited to these. As aforesaid, the absorptive wavelength for any given ophthalmic lens depends on among other things, material of construction, additives and the like. Thus the scope of absorptive wavelength can include wavelengths as high as 120000 nm and the modifications needed to implement these would be readily understood to the artisan given the present description. For example, for wavebands from about 400 nm to about 1000 nm, the only component requiring change would be the bandpass filter, e.g. instead of a UV filter, a visible or rear infrared bandpass would be used.. Any imaging lens re-optimization or changes in focus setting for this regime would also be readily understood, and indeed various commercial cameras are more efficient at 1000 nm than 355 nm. Beneficially, the imaging lens could also be fabricated from less expensive materials for wavelengths up to about 2000 nm. After 1000 nm (e.g. from about 1000 nm to about 5000 nm), an infrared imager rather than a camera would be required, as would be appreciated by the artisan. Up to about 5000 nm, this would include InSb or PtSi. Required filter changes would track these to wavelength changes; and conventional strobe lamps would be replaced by a black body source or infrared laser. The imaging lens would in this, region be Ge or the like as understood by the artisan. Above 5000 nm (e.g. about 5000 nm to 12000 nm) the camera would be MgCdTe or the like; the imaging lens could still be Ge.

In another embodiment of the invention, the light that illuminates the ophthalmic lens under inspection is configured to strike the lens at an angle of incidence that is nearly normal (perpendicular) to the surface of the lens being struck. As employed in this specification, the term "substantially normal," "nearly normal," "nearly perpendicular" and the like mean the incident light is perpendicular (90°±30°) to any point on the convex or concave (preferably convex) surface of the ophthalmic lens being illuminated. Thus, without limitation, in one embodiment, the incident light is incident at an angle of about 60° (90°±30° off the normal); and another embodiment the incident light is incident at an angle of about 68° (or ±22° off the normal). This is true even if the ophthalmic lens has a curved topography, e.g. the bowl-shaped appearance of a soft contact lens which consists of a convex side and a concave side, the convex side typically being illuminated for inspection purposes, although the present invention contemplates illumination of the concave surface as well. In a particular practice of the inventions one or more optical components that affect ray path in this regard are interposed between the light source and the ophthalmic lens being inspected such that the light striking the ophthalmic lens is nearly normal to the entire curved surface thereof upon which it is incident. For example, nearly normal incidence can be achieved by providing a short focal length group of optical elements as the last set in the illumination path for the convex side of the lens. Alternatively, to provide nearly normal incidence for the concave side of the lens, a different configuration of optical elements would be required; for example, a negative focal length group of optical elements could be used as the last element in the illumination path. In another preferred illumination practice, the incident light is caused to be attenuated near the center of the ophthalmic lens being inspected, especially where said lens has gradations in thickness due to design, rather than cosmetic flaws. In another embodiment especially suited for toric lenses, a bull's eye pattern is produced using a diffractive holographic element. This pattern permits more intense incident light to be focused on the periphery of the toric lens (e.g. 10 times the intensity at the periphery relative to the intensity at the center of the toric lens) with quick drop off where the lens ends (e.g. 10 times less intensity immediately outside the perimeter of the toric lens). This bull's eye configuration utilizes the incident light more efficiently and prevents light passing through the flange of the front curve from saturating the image generated.

The invention is further directed to a carrier for ophthalmic lenses under inspection, the carrier preferably has a frustroconically shaped well extending therethrough, the sides of the well having specific angularity to accommodate the ray path of light travelling at an angle of incidence nearly perpendicular to the entirety of the curved surface of an ophthalmic lens. Alternatively, an eyeball-shaped carrier can be used, e.g. if the light is incident on the concave side of the lens.

Illumination in the invention can be stroboscopic, as, in the case where a plurality of ophthalmic lenses are being inspected in a continuous fashion.

In regard to: detecting step (b):

In the invention, the image that is detected in step (b) is detected using only the light at the absorptive wavelength, where that light has managed to be transmitted through the ophthalmic lens for the reasons previously stated. Step (b) contemplates the use of an imaging sensor, such as a CCD pixelated image sensor, e.g. a camera with a CCD chip, a CID sensor or film, the imaging device having sufficient spectral response to light at the absorptive wavelength as hereinbefore defined (e.g. up to 400 nm, or at least about 700 nm). That is, the imaging sensor must have a quantum efficiency sufficient to capture an image within this wavelength range. The imaging lens assembly employed with said sensor must also have transmission characteristics appropriate for transmitting the absorptive wavelength, be it for example in the ultraviolet infrared range. Preferably, a filter coating as known in the art correlating to the absorptive wavelength of the illuminating light (e.g. a UV filter coating applied when the wavelength is up to, about 400 nm) is applied to the imaging lens assembly (e.g. the final surface of the lens assembly).

In one embodiment of the invention, the imaging lens assembly has a flat focal surface. In a preferred embodiment, where the ophthalmic lens being inspected has a curved topography, as e.g. in a soft contact lens which has a concave (back) side and a convex (front) side, the preferred imaging lens assembly has a curved focal surface. This allows the entire curved ophthalmic lens under inspection to be imaged with improved focus on the flat image plane of the camera chip at one time without requiring multiple cameras or sacrificing resolution. In the preferred embodiment, the curvature of the focal surface of the imaging lens assembly should be substantially equal to the average curvature on the concave side of the ophthalmic lens being inspected. In another embodiment of this practice, particularly useful where artifacts of inspection interest occur on the back side of an ophthalmic lens, the curvature of the focal surface of the imaging lens assembly is substantially equal to both the front and back sides of the ophthalmic lens; in an alternate embodiment, the imaging lens assembly is designed to have sufficient depth of focus across the field so that artifacts on the front side of the ophthalmic lens can be imaged as well as artifacts on the back side of' said lens. In one practice of this embodiment, where the distance between the ophthalmic lens being inspected and the first surface of the imaging lens assembly is at least about 30 mm, the imaging lens assembly is provided in the form of a specific imaging lens system, described hereinafter. For the preferred embodiment, the light is incident on the convex side of the ophthalmic lens and the imaging lens assembly is on the concave side of the ophthalmic lens, but the invention also contemplates the opposite configuration where the light is incident on the concave side of the ophthalmic lens and the imaging lens assembly is on the convex side of the ophthalmic lens, which configuration one of ordinary skill in the art could implement based on the teachings herein. The present invention also contemplates various lens assemblies as aspects thereof.

In practice, the imaging sensor utilized in the invention can include a digital camera as known in the art which can be adapted to meet or optimize the optical requirements delineated herein.

In regard to analyzing step (c):

Variations in light at the absorptive wavelength that happen to be transmitted through the ophthalmic lens, as detected by the imaging sensor, are caused by changes in thickness that translate into cosmetic flaws of interest to and important for lens inspection; or that translate into deliberate design features, such as toric thin zones, that need to evaluate against design specification. Because the invention suppresses unimportant lens detail in the first instance, the image is easier to analyze since this unwanted information need not be extracted at the image analyzing stage. Easier analysis is also due to the fact that in practice, the image generated consists of lighter details over a darker background. Because the image is simplified, conventional analysis techniques can be adapted.

Inspection pursuant to the invention can be practiced at any point in the lens production process where the ophthalmic lens is already formed. Without limitation, the invention can be practiced in the case of soft contact lenses while the lens is still in the front curve mold (female mold half) of the production process. The molds in this regard are typically constructed from the plastics identified hereinabove for this purpose, and have a relatively high transmittance for light in the UV wavelength that constitutes a representative absorptive wavelength for HEMA-based soft lenses containing a UV absorber. Advantageously, the lens at this point is already immobilized in a rigid carrier, hence facilitating precise positioning for inspection. The ophthalmic lens can also be inspected in accordance with the invention when it is in its final packaging, which is typically translucent. Inspection in the final package can provide more uniform images inasmuch as the lighting is typically more uniform; and final packaging inspection can also identify cosmetic flaws caused by transfer of the lens to the final package. In another aspect of the invention, a specific imaging lens assembly is contemplated when the opthalmic lens is immersed in a fluid, such as the saline solution of its final packaging, the illumination light used in regard to this particular lens assembly specifically including the visible spectrum; the lens assembly in this regard is especially tolerant to positioning errors to which a floating ophthalmic lens is otherwise prone.

The following specific practices of the invention are now described with reference to the drawings. While illustrative of specific embodiments, the invention is not limited thereto.

FIGS. 1A, 1B and 1C illustrate the layouts of three different embodiments contemplated by the invention: FIG. 1A illustrates an embodiment of a first illumination practice of step (a) of the invention where a conventional light source is filtered to obtain light at an absorptive wavelength which then illuminates the ophthalmic lens. FIG. 1C illustrates another embodiment of this first practice wherein a laser is used to generate light at the absorptive wavelength in the first instance. FIG. 1B illustrates an embodiment of a second illumination practice of step (a) wherein the ophthalmic lens is illuminated with a conventional light source that provides light having both an absorptive wavelength and transmittable wavelengths, the light that is transmitted by the ophthalmic lens is then filtered thereafter to provide only absorptive wavelength to the imaging camera.

In FIGS. 1A, 1B and 1C, the system shown generally comprises illumination subsystem 10, imaging subsystem 12, and image processing subsystem 15. But for illumination subsystem 10 in FIG. 1C utilizing laser 16, the subsystems can be as generally disclosed in U.S. Pat. No. 5,500,732, incorporated by reference herein, as modified to effectuate the present invention.

In FIG. 1A, illumination subsystem 10 comprises light source 11 which can be a conventional lamp such as a xenon lamp, including preferentially a stroboscopic flash lamp to enable continuous high speed inspection. The light 17 emitted by lamp 11 contains as a major component wavelengths that are transmittable by ophthalmic lens 22. However, the spectral distribution of lamp 17 also includes wavelengths that are absorptive to ophthalmic lens 22, which can comprise HEMA and a NORBLOCK additive. That is, light 17 from lamp 11 contains light of a wavelength up to 400 nm, including in particular sufficient wavelength output in the range between about 300 nm to about 360 nm. Filter 18, which can be a UV bandpass filter or series of filters, is interposed between light source 11 and ophthalmic lens 22 being inspected. Filter 18 filters the light 17 output by source 11 to obtain light 19. Light 19 preferably consists essentially of light at the absorptive wavelength, e.g. about 330 nm to about 360 nm, preferably from about 340 nm to about 350 nm. Light 19 illuminate ophthalmic lens 22. Light that is transmitted by ophthalmic lens 22, either because it was not totally absorbed by lens 22 or because of cosmetic flaws in lens 22, is identified as light 20. Light 20 is detected by camera 13a having imaging lens assembly 14. Signals generated by camera 13a, including changes in intensity within light 20, are processed by image processing subsystem 15, which analyzes the image of lens 22 for these intensity changes, hence identifying cosmetic flaws in lens 22 whereupon the lens can be rejected. If imaging lens assembly 14 is not chromatographically corrected, the light can be narrowed to a bandwidth of about 12 nm centered around e.g. about 340 nm using an appropriate bandwidth filter (not shown). Ophthalmic lens 22 is situated in a container (e.g. its front curve polymerization mold or its final packaging) that is in a well extending through a lens carrier (not shown). In practice, the lens carrier can be located on conveyor or a rail guide to effectuate continuous movement of the lenses through the inspection station, thus providing a high speed inspection process.

Figure 3:
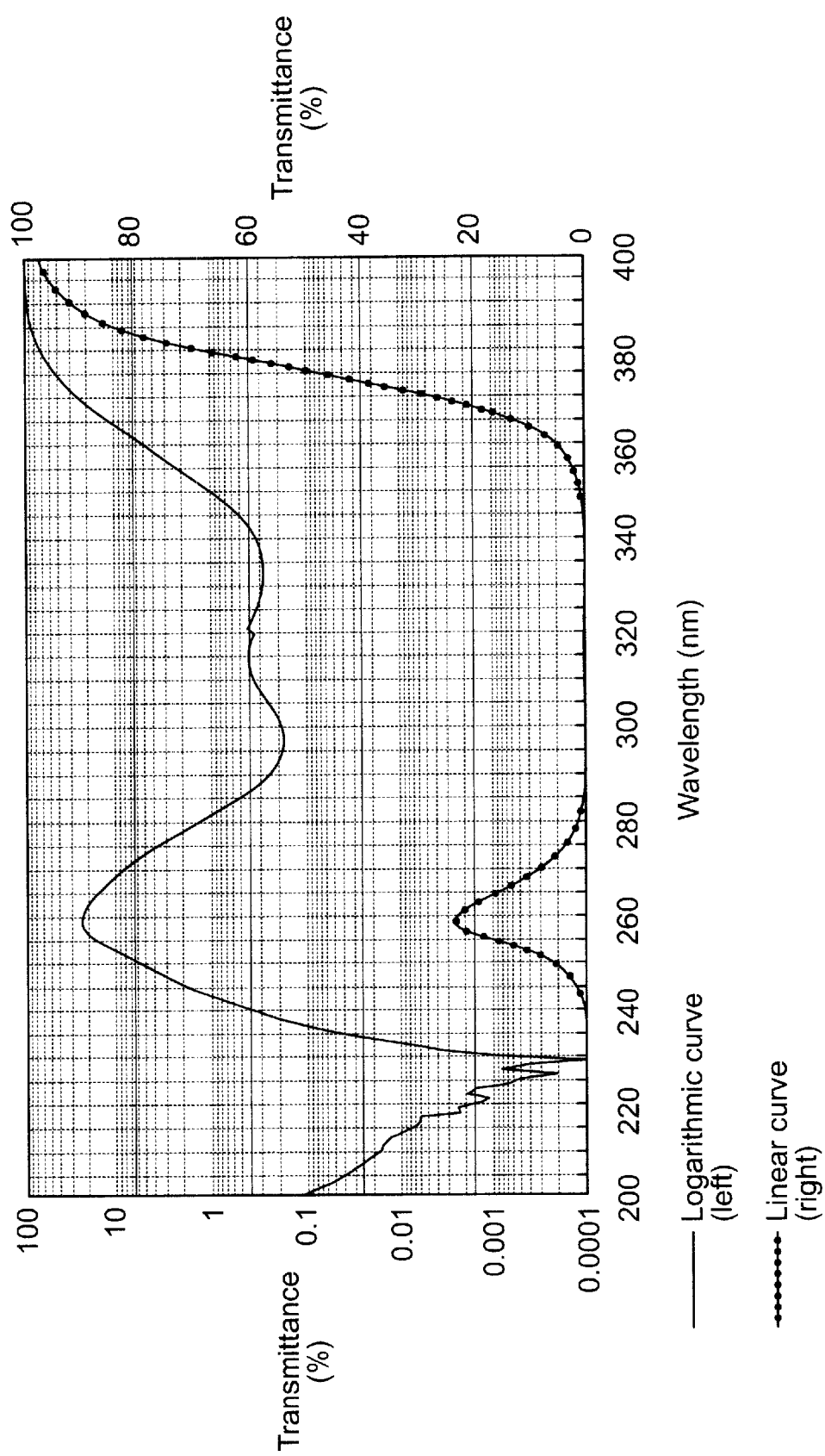
FIG. 3 shows graphical depictions of the spectral transmittance of a soft contact lens (−1.00D power) having incorporated therein a commercially available ultraviolet absorption additive; the left scale is logarithmic; the right scale is linear. The log scale shows detail in the high absorption area.

In the embodiment shown in FIGS. 1A, 1B and 1C, lens 22 is a HEMA-based soft contact lens that has a NORBLOCK UV absorber therein. The absorption spectra for a −1.00 power HEMA-based soft contact lens that contains NORBLOCK in an amount of about 1 part NORBLOCK per hundred parts HEMA is shown in FIG. 3. As indicated in FIG. 3 the area of greatest absorption is at a wavelength of about 280 nm to about 360 nm.

In FIG. 1B, light source 11 and light 17 are as hereinbefore described. In FIG. 1B, however, light 17 from light source 11 illuminates ophthalmic lens 22 directly, without any intervening filtering to the absorptive wavelength as in FIG. 1A. In FIG. 1B, light transmitted by ophthalmic lens 22 is identified as 21 and consists of those wavelengths in light 17 to which it is effectively transparent, and those wavelengths to which it is absorptive, the latter being transmitted at vastly reduce intensity (e.g. to the transmittance percentages as hereinbefore described), if at all, or transmitted because of cosmetic flaws. In the embodiment shown in FIG. 1B, light 21 is filtered by filter 26 which can be a bandpass filter or series of filters constituted to transmit only light at the absorptive wavelength, i.e. light 23. Camera 13a thereafter detects light 23, the imaging and processing as heretofore described.

In FIG. 1C, the light source is laser 16 and ophthalmic lens 22 is illuminated by light 24 generated therefrom. Laser 16 is operated such that it emits light 24 at the absorptive wavelength in the first instance. In preferred embodiments described hereinafter, various optical components, such as beam expanders, apodizers, diffusers and the like can be interposed between laser 16 and ophthalmic lens 22 to account for the Gaussian nature of the laser beam (e.g. narrow, and more intense at the center of the beam) and transform it in terms of intensity and pattern to account for corrective thickness profiles (e.g. toric-shaped ophthalmic lenses) and curvature extant in ophthalmic lens 22 to thus more effectively and evenly illuminate same. In FIG. 1C, ophthalmic lens 22 is shown having a convex side 22a and a concave side 22b, which exemplifies the use of these terms in this specification. In yet still another preferred embodiment described below, laser light 24 is configured such that it illuminates lens 22 at angles of incidence that are substantially normal (perpendicular) to the entire convex surface 22a of lens 22 facing the illuminating laser light. In one practice of this embodiment described below, a special lens carrier subject of the instant invention is employed to facilitate the perpendicular angles of illumination. Light 25 exiting ophthalmic lens 22 from its concave surface 22b is then transmitted to imaging subsystem 12. In FIG. 1C the camera 13a and imaging lens assembly 14 and processing system 15 are as heretofore described.

Figure 5:
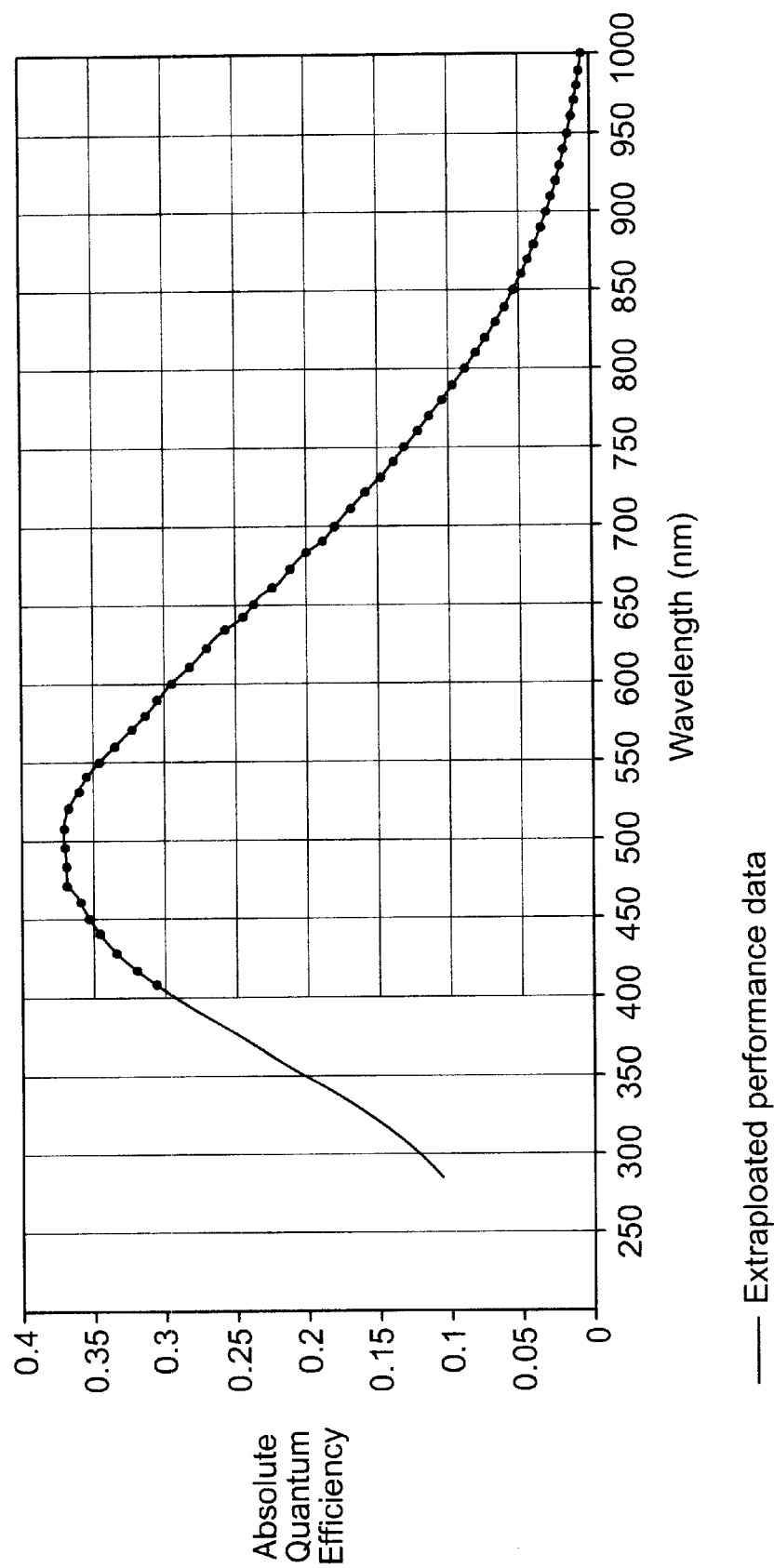
FIG. 5 is a graphical depiction of the quantum efficiency of a commercially available camera chip used in an embodiment of the invention, showing extrapolated performance data in the UV region of interest.

FIG. 2 is a detailed illustration of a preferred embodiment of the layout shown in FIG. 1A. In FIG. 2, light source 11 is a 2.2 kilowatt, 40 joule Hg—Xe stroboscopic flash lamp having a 25 mm long emission area and a metal parabolic reflector 11b. Condenser 11a gathers light emitted from the light source (light 17 in FIG. 1) to afford higher energies of illumination; a condenser of this type includes an M-G SYMMETRIC CONDENSER, O1 CMPI19, commercially available. Ophthalmic lens 22 comprises HEMA and NOR-BLOCK ultraviolet additive. Filter 18 is a UV bandpass filter (e.g. CORION p10–340 Dielectric Filter) and filters light 17 to an absorptive wavelength of about 330 to about 360 nm. The filtered light (light 19 in FIG. 1) is transmitted through ophthalmic lens 22 and emerges from lens 22 (light 20 in FIG. 1) which is detected by camera 13a having imaging lens assembly 14. Camera 13a can be comprised of a digital camera known in the art such as a Kodak ES-1, the spectral response for which is shown in FIG. 5. As indicated in FIG. 5, the ES-1 has sufficient quantum efficiency at wavelengths up to about 400 nm, including about 300 nm to about 360 nm, to capture an image of transmitted light 20. Imaging lens assembly 14 comprises a quartz lens having the following specifications:

Lens construction: 3 group 3 element, all quartz lens
Wavelength: 266 nm
Focal length: 25.04 mm +/−5%
Back focal: 22.07 mm +/−5%
Flange back: 17.526 mm C-mount
Aperture ratio: f/2.8 +/−5%
Image size: $\phi$16 (9.6×12.8)
Angle of view:
  Image to object distance=infinity
    Diagonal: 37.2°
    Horizontal: 29.7°
    Vertical: 22.2°

OPT. Distortion: −4.05% (diagonal)
Aperture of front lens: $\phi$12.0
Aperture of rear lens: $\phi$10.0

Figure 4:
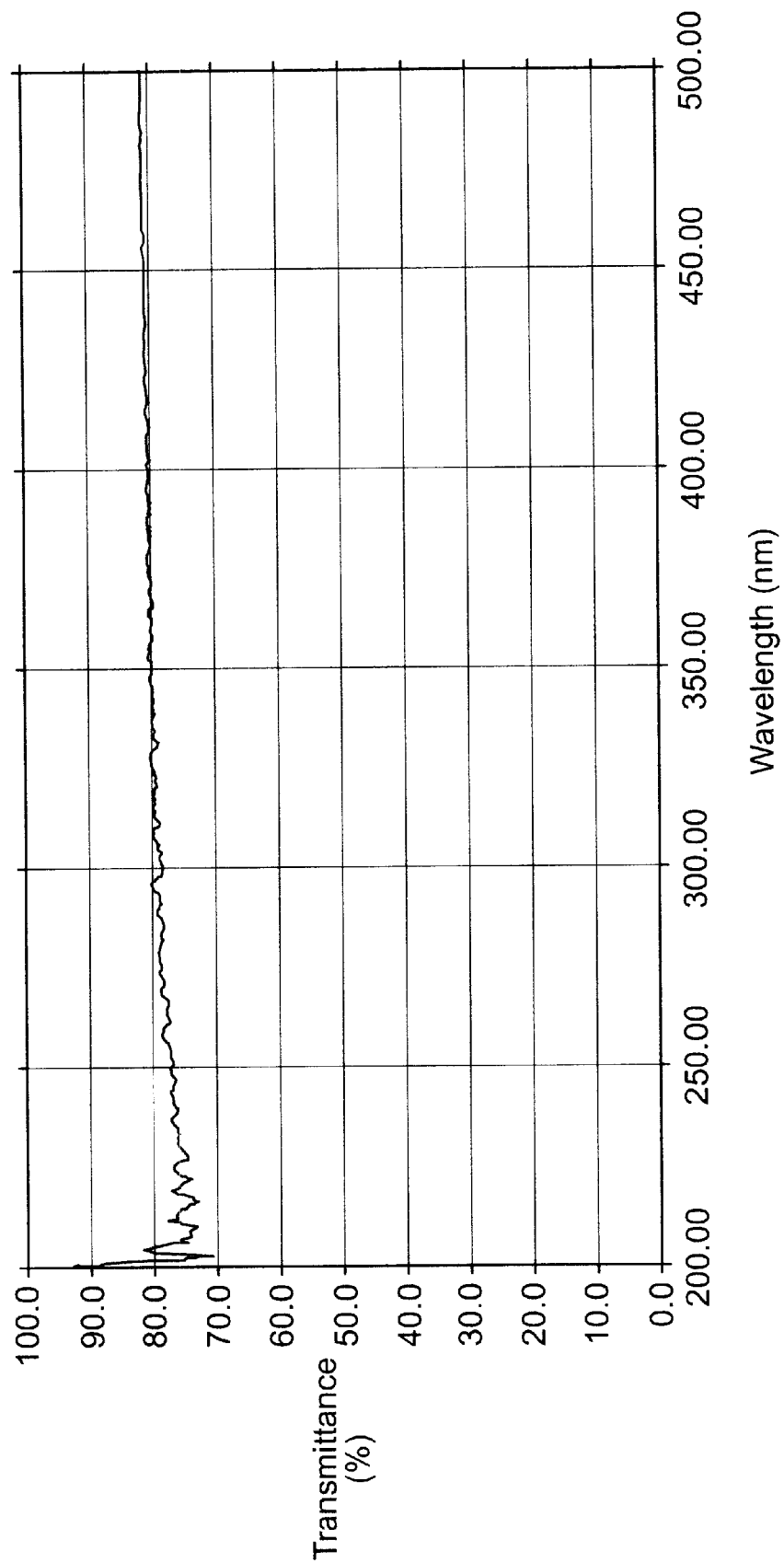
FIG. 4 is a graphical depiction of the spectral properties of a lens used in an imaging camera in an embodiment of the invention.

Such a lens is available from UNIVERSE KOGAKU (AMERICA) INC., 25 mm F/2.8 UV CCTV lens. The spectral properties of this lens are shown in FIG. 4, which indicates sufficient lens transmission to light at wavelengths down to about 200 nm. In a preferred embodiment, lens assembly 14 is coated with an appropriate available filter coatings, such as an anti-reflection coating and/or a UV bandpass/shortpass coating, to enhance the imaging of light transmitted through ophthalmic lens 22 and dampen extraneous light that may find its way into the system.

The imaging lens assembly 14 as described above has a flat focal surface. In another embodiment, imaging lens assembly 14 has a curved focal surfaced which improves the image that is obtained for curved ophthalmic lens 22 on the flat imaging plane of the camera chip in camera 13a. The optical layouts of various imaging lens assemblies in this regard are shown in FIGS. 6, 9, 10 and 11.

FIG. 2 shows transport subsystem 28 which conveys ophthalmic lens 22 or a plurality of such lenses through the inspection system defined by the layout. Lens 22 can be situated in a container (e.g. its polymerization mold, such as the front curve part of same; or its final packaging) that is in a well preferably extending through lens carrier 27. Lens carrier 27 in turn is situated on conveyor 29 which can begin the form of a rail guide for continuous movement of lens 22 when in its final packaging containing saline solution.

FIG. 2 also illustrates the detail for a preferred practice of the layout shown in FIG. 1B, only instead of filter 18, filter 26 is employed. Filter 26 as shown is interposed after ophthalmic lens 22 but before imaging subsystem 12. An example of a suitable filter in this regard is commercially available CORIAN "hot" 350 nm P1O-350F.

Figure 7:
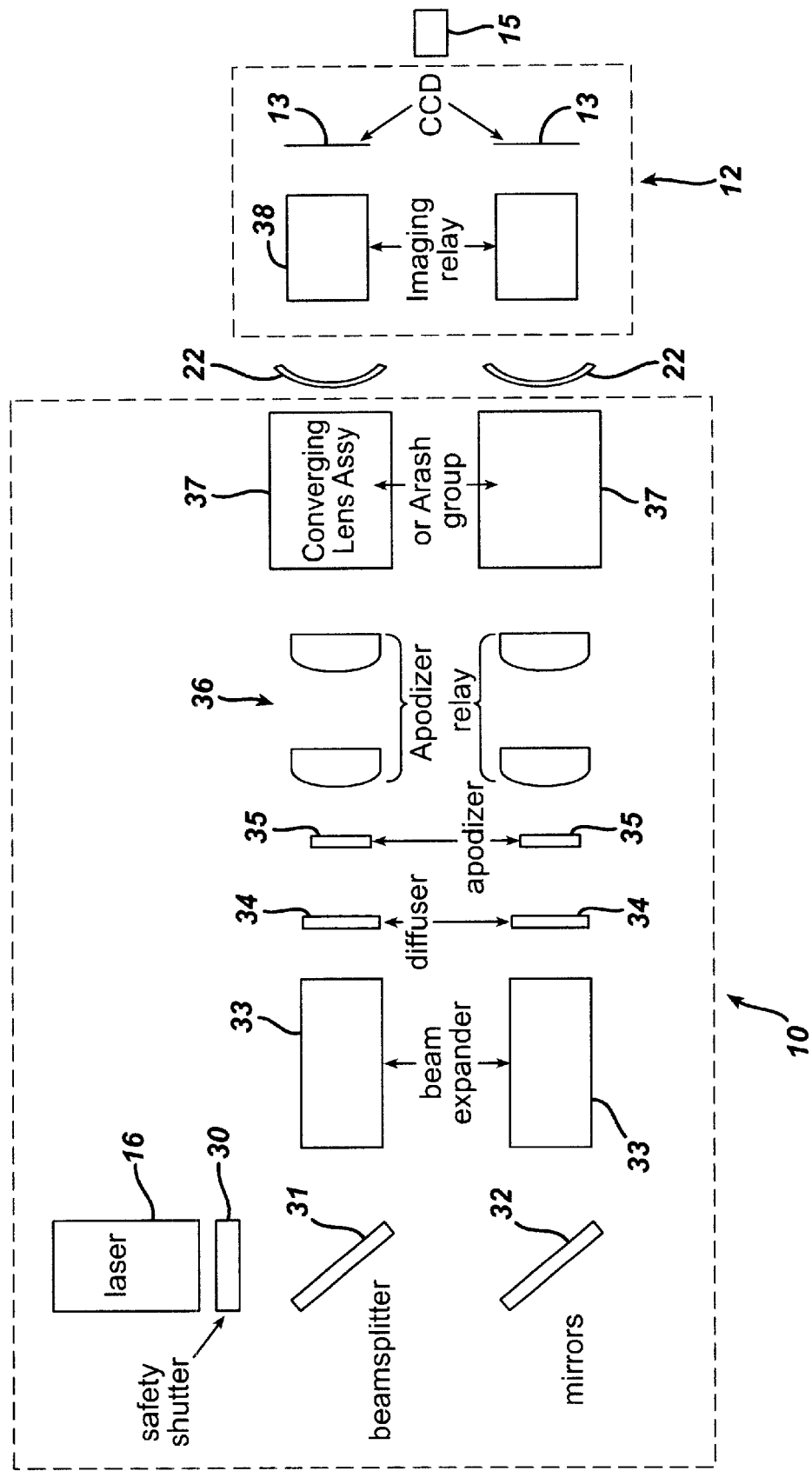
FIG. 7 is a block diagram showing a flow layout for an inspection embodiment of FIG. 1C employing a laser light source.

FIG. 7 is a block diagram illustrating details of a preferred embodiment of the layout shown in FIG. 1C. The layout shown in FIG. 7 generally comprises illumination subsystem 10, imaging subsystem 12 and image processing subsystem 15. In this embodiment, illumination subsystem 10 comprises a laser light source 16 which generates light at a wavelength absorptive to ophthalmic lens 22, including wavelengths up to about 400 nm, preferably a monochromatic wavelength. For example, laser 16 can emit a monochromatic laser wavelength of about 355 nm, commercially available as NEW WAVE MINI LASE III with wide body, vertical option. The light from laser 16 passes through shutter 30 (from UNIBLITZ) and impinges upon one or more beam splitters 31 to divide the laser beam into multiple working inspection beams, and one or more mirrors 32 to direct the beams onto a predetermined path; the subsystem further includes one or more beam expanders 33 (available as CVI Q EXPANDER;

BXUV-4.0-5X-355). One or more diffusers 34 are interposed to provide a real object, at the filter plane for the illumination subsystem, to project to imaging subsystem 12. To optimize the efficiency of the system the diffusing angle may be chosen to match the collection angle of the imaging lens in imaging subsystem 12, e.g. a 6 degree to 20 degree diffuser can be employed; a diffuser of about 10 degrees is preferred (e.g. 45311 Diffuser, 10 degree from P.O.C. L5DKITCN 10–50 mm Edmuund #54493). One or more apodizers 35, typically one or more selectively absorptive filters, are employed to transform the Guassian output of the beam expander 33, which is more intense at the beam center, to a profile adapted to the transmission profile of ophthalmic lens 22. For example, in certain instances, ophthalmic lens 22 has a thickness profile associated with its corrective powers, e.g. minus power lenses are thicker at the periphery of the lens than in the middle. Other types of ophthalmic lenses, e.g. positive power lenses, are thicker in the middle than in the center, for which types of lenses the apodizer 35 would be switched out of the optical path. These thickness variations affect the transmission of light at the absorptive wavelength, since the more lens material the light has to traverse, the more intense (or brighter) the light need be at these areas. Since lasers are generally more intense at the center of their beams, the presently described system of optical components is employed to transform the beam to suit the thickness profile of the ophthalmic lens, thereby facilitating improved imaging of same.

Figure 13:
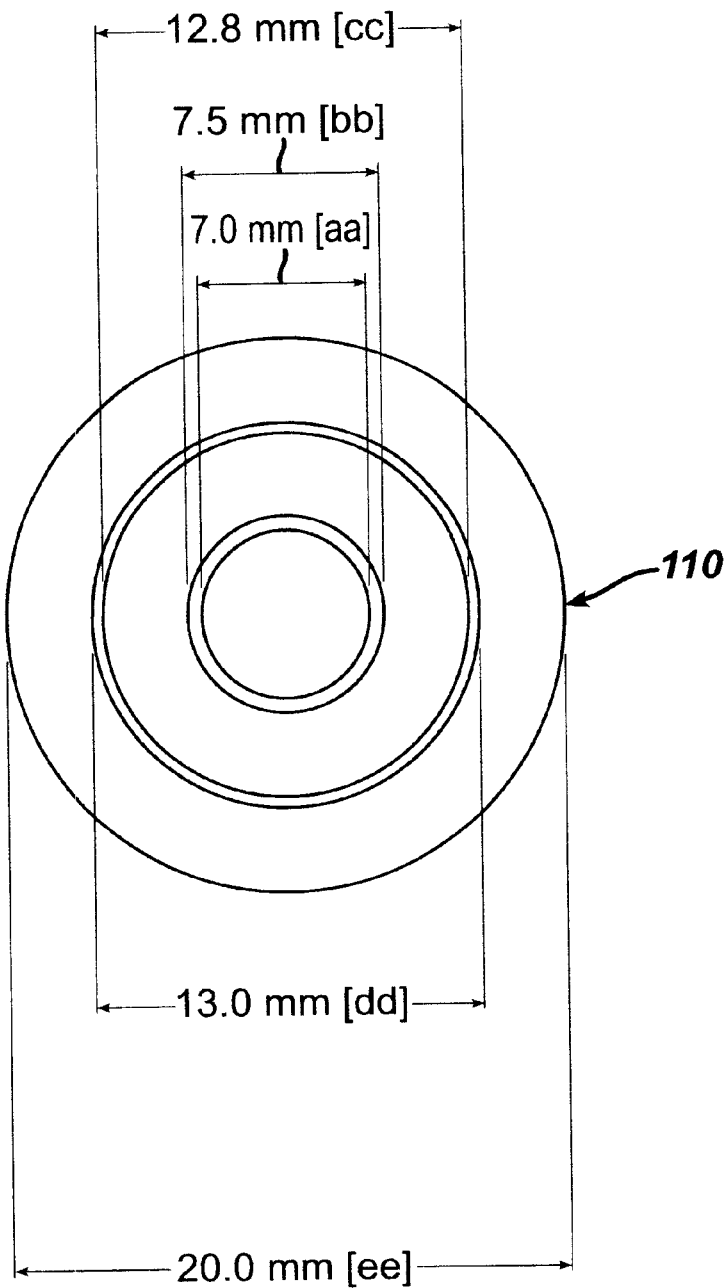
FIG. 13 illustrates aspects of an apodizer of the invention.

In an embodiment of the present invention, apodizer filter 35 has a bull's eye pattern, an example of which is shown in FIG. 13. In FIG. 13, apodizer filter 110 is shown having various zones characterized by transitions in optical density (OD).

In FIG. 13 the OD's indicated are logarithmic; that is, in FIG. 13, an OD=1 means $1/10^{th}$ of incident light is transmitted therethrough; an OD=2 means $1/100^{th}$ of incident light is transmitted therethrough; an OD=3 means $1/1000^{th}$ of incident light is transmitted therethrough. As seen in FIG. 13, apodizer 110 is comprised of a central circular area "aa;" a first annular area "bb" surrounding "aa" and substantially concentric therewith; a second annular area "cc" surrounding "bb" and substantially concentric therewith (area "cc" also referred to herein as a middle area); and a third annular area "dd" surrounding "cc" and substantially concentric therewith (area "dd" also referred to herein as a peripheral area). In the embodiment illustrated, the central area "aa" of apodizer 110 is 7 mm in diameter and has an OD=1. Transmission increases in section "bb" ringing center "aa", the OD transitioning from 1 to 0. Outwardly thereafter, the OD transitions in middle area "cc" from 0 to 3 and remains at an OD=3 throughout the peripheral area "dd" (the outer 3.5 mm). Hence, for apodizer 110 transmitted light is, averaging the transitions, approximately 10 times more intense in middle area "cc" (13 mm diameter) than in central area "aa" (7 mm diameter); and approximately 10 times less intense in peripheral area "dd" (20 mm diameter) than in area "cc." In yet another embodiment of the invention, the bull's eye pattern of the apodizer may be produced using a diffractive holographic element which utilizes the incident light more efficiently.

In FIG. 7, the beam output from apodizer 35 is transmitted to apodizer relay system 36 (KPX082, Bk7, 50 mm f.1). Converging lens assembly 37 consists of a series of positive power lenses which converge and modify the path of the illuminating light such that it strikes the convex surface of ophthalmic lens 22 which faces said light at an angle of incidence that is substantially normal over to the entire convex surface. As shown in FIG. 7 an imaging relay system 38 consisting of a system of optical relay lenses is used to reconverge the light after it has been transmitted through and exits the concave side of ophthalmic lens 22. The imaging relay system 38 collects and directs the emerging light such that it is substantially normal to the center of lens 22 whereafter it is transmitted to imaging sensor 13, e.g. a CCD camera.

Figure 8:
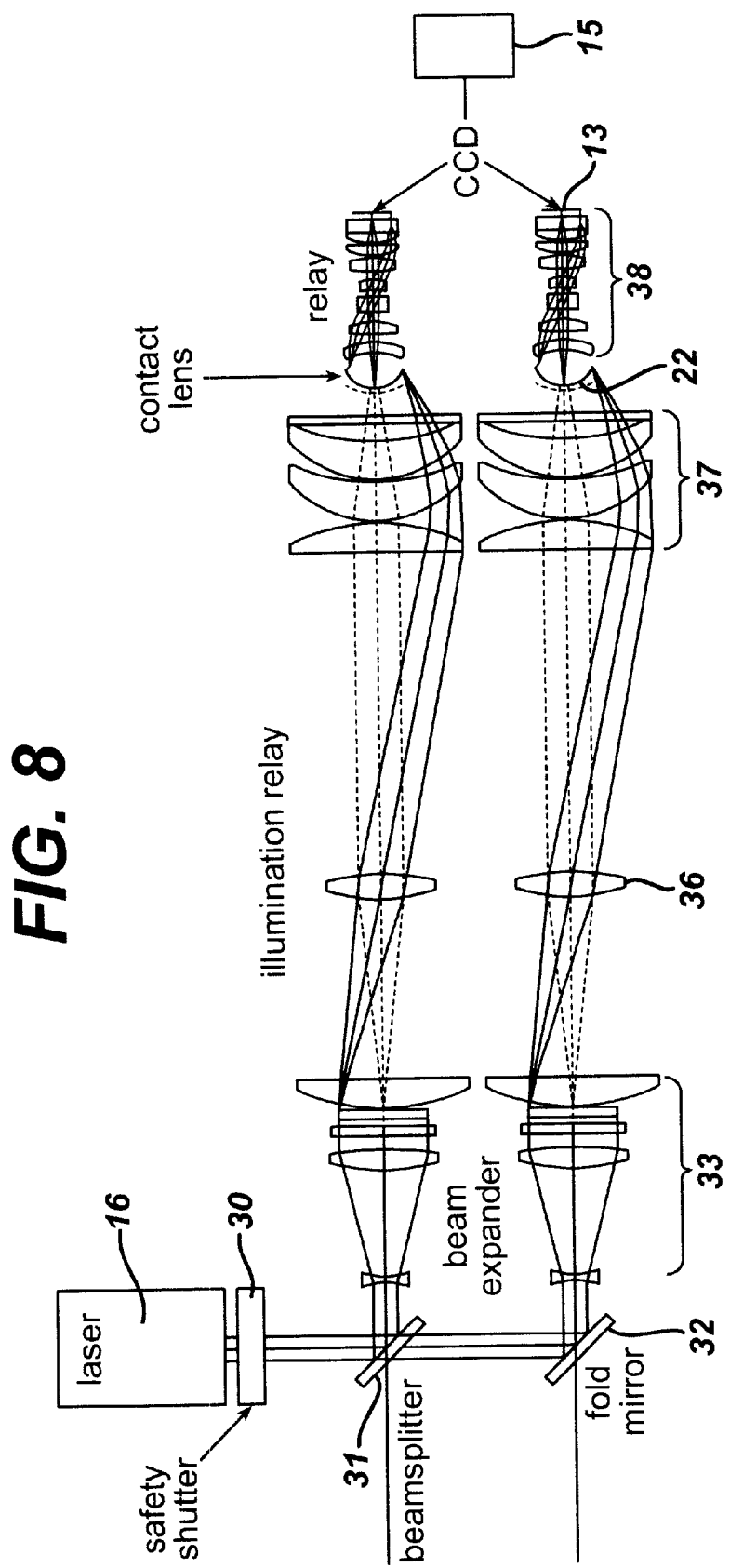
FIG. 8 is a diagram showing various lens elements and light ray paths of the layout in FIG. 7.

FIG. 8 shows a detail of various lenses in FIG. 7 and the ray path of light travelling through the system illustrated in FIG. 7. A detail of the imaging relay system 38 contemplated as an aspect of the present invention is shown in FIGS. 6, 9, 10 and 11.

In the lens assemblies described herein, certain lens shapes and optical configurations are set forth. These are representative only, and modifications such as changes in radii, number and shape of optical elements to accomplish the imaging goals stated herein are all contemplated as within the scope of the present invention.

Figure 6:
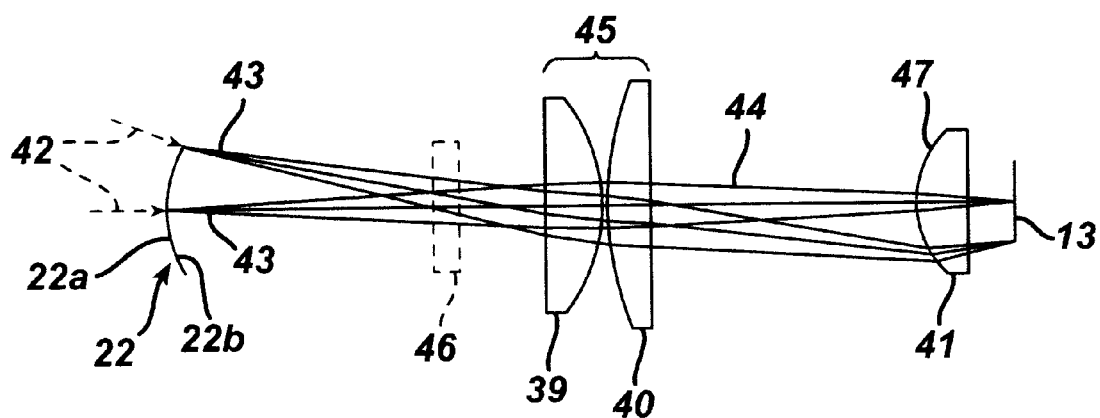
FIG. 6 is a diagram showing an embodiment of an imaging lens assembly of the present invention which images a curved object, such as an opthalmic lens, onto a flat image plane.

FIG. 6 illustrates an embodiment of an imaging lens assembly contemplated by the present invention to image a curved object, e.g. ophthalmic lens 22 which is steeply curved, i.e. its concave surface 22b is facing, i.e. lens 22 is curved concave toward, said relay lens assembly. Without limitation, concave surface 22b has a radius of curvature in this regard of between about 6.5 mm to about 9 mm; about 7.7 mm being typical, onto a flat image plane 13. In FIG. 6, illuminating light 42 strikes the convex side 22a of ophthalmic lens 22 at angles of incidence that are substantially normal over the entire convex surface of 22b. The light emerging from the concave surface of ophthalmic lens 22b is divergent, with some scattering distributed around the exit angle which is approximately the same as the entrance angle. The lens assembly in FIG. 6 comprises a relay lens element 45 preferably formed of first and second planoconvex lenses 39 and 40 which converge divergent light 43 to form light 44. In the embodiment shown, lenses 39 and 40 provide most of the optical power for relaying an image of the curved ophthalmic lens 22 onto flat image plane 13. Light 44 is transmitted to a field flattening lens element 41 (which is illustrated as a single lens but can be a multiplicity of lenses) which is very highly positively powered. Without limitation, field flattening element 41 is preferably a third planoconvex lens having a steeply curved convex surface 47 on which light 44 is incident whereafter 41 focuses light 44 from relay lens element 45 onto flat imaging plane 13. In the practice illustrated, convex surface 47 has a radius of about 8 mm to about 12 mm although the radius can change, e.g. if multiplicity of lenses are used for 41. Field flattening lens 41 has a very short focal length relative to flat image plane 13; the focal length of lens 41 is preferably about 5 mm to about 100 mm, more preferably about 10 mm to about 50 mm; still more preferably about 20 mm. In another preferred practice, an aperture stop 46 is interposed between ophthalmic lens 22 and relay lens element 45. The lens assembly shown in FIG. 6 is capable of a long working distance, e.g. the distance from lens 39 to ophthalmic lens 22 can be at least 30 mm.

Figure 9:
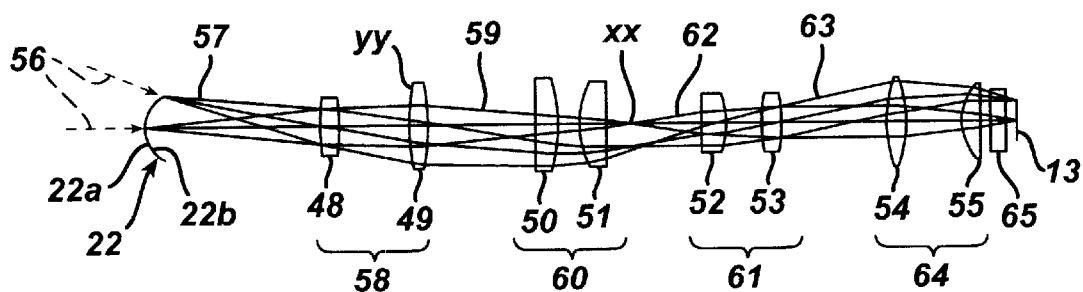
FIG. 9 is a diagram showing an embodiment of another imaging lens assembly of the present invention.

FIG. 9 illustrates another embodiment of an imaging lens assembly contemplated by the invention to image an object having a steeply curved surface onto a flat imaging plane. In FIG. 9, two relay lens elements are employed; an intermediate image (first image) of lens 22 is created from the first relay lens element, which intermediate image is relayed to the second relay lens element then onto the flat image plane for sensing. The image of ophthalmic lens 22 is thus imaged twice. In doing so, and in order to have a long working distance, i.e. the distance from ophthalmic lens 22 to the first lens component in the first relay, the angles of incidence of light passing through ophthalmic lens 22 over the field of view can be relatively small. The second relay lens element provides additional field flattening power needed to obtain the flat image plane as imaged by steeply curved ophthalmic lens 22. In FIG. 9, ophthalmic lens 22 has convex surface 22a and convex surface 22b with radius of curvature as described in FIG. 6. Illuminating light 56 strikes convex surface 22a at angles of incidence that are substantially normal over the entirety of surface 22a. Light transmitted through 22 emerges from concave surface 22b as divergent light 57. The lens assembly in FIG. 9 comprises a first relay lens group 58 preferably comprised, of a first relay lens component 48 located at the aperture stop of the assembly and a second relay lens component 49 which converge divergent light 57 to form light 59. Without limitation, second relay lens element 49 preferably has an aspherical surface on the side denoted "yy." This aspherical surface provides for a higher level of optical performance and high image quality by minimizing the on-axis as well as some of the off-axis aberrations such as spherical aberration, coma and astigmatism. Light 59 is transmitted to field lens group 60 preferably comprised of first and second planoconvex lenses 50 and 51. Field lens element 60 serves two functions: it effectively serves as adjuncts to the first relay lens element 58 and concurrently serves as a field lens which directs the off-axis light into the second relay lens element 61. Thus field lens group 60 collects light 59 that is at the periphery of said field of view. Field lens element 60 focuses light 59 to form a first image of ophthalmic lens 22 at first image plane XX. Aft of first image plane XX, the light transmitted by field lens element 60 is divergent, represented by light 62. A second relay lens element 61 is preferably comprised of planoconvex lens 52 and equiconvex lens 53 which partially collimate divergent light 62. Partially collimated light 63 is transmitted to a field flattening lens element 64 which is very highly positively powered. Field flattening lens element is preferably comprised of second equiconvex lens 54 and third planoconvex lens 55, both of which are positively powered, and focuses partially collimated light 63 onto flat imaging plane 13. Positively powered lens element 55 has a very short focal length relative to flat image plane 13. The focal length of lens component 55 in this regard is preferably about 5 mm to about 10 mm; more preferably about 10 mm to about 50 mm; still more preferably about 20 mm. In another preferred embodiment optical filter 65, is interposed between lens component 55 and flat image plane 13. The lens assembly shown in FIG. 9 is capable of a long working distance, i.e. the distance form first relay lens component 48 to ophthalmic lens 22 can be at least 30 mm. The two relay assembly shown in FIG. 9 provides a high level of optical performance with a long working distance as well as a small angle of incidence of the rays passing through ophthalmic lens 22 being imaged. As indicated previously, modifications to the optical configurations described herein are contemplated as being within the scope of the invention, including without limitation, modifications to radii, the number of optical elements and the like.

Figure 10:
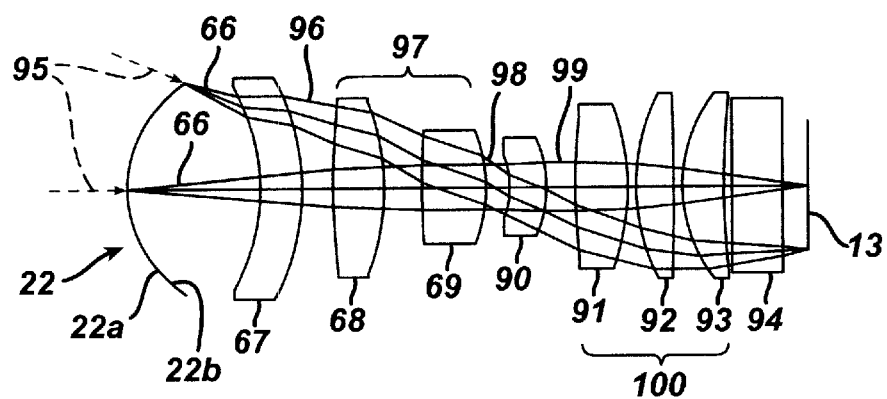
FIG. 10 is a diagram showing an embodiment of yet another imaging lens assembly of the invention.

FIG. 10 illustrates yet another embodiment of an imaging lens assembly contemplated by the present invention to image an object having a steeply curved surface onto a flat image plane. The lens assembly illustrated in FIG. 10 is relatively compact and the working distance of which said lens assembly is capable of is relatively short. In FIG. 10, ophthalmic lens 22 has a convex surface 22a and a concave surface 22b which is directed toward the lens assembly and the flat image plane; the radius of curvature of lens 22 is as described in FIG. 6. Illuminating light 95 strikes convex surface 22a at angles of incidence that are substantially normal over the entirety of surface 22a. Light transmitted through ophthalmic lens 22 emerges from concave surface 22b as divergent light 66. Divergent light 66 is incident on first astigmatic corrective lens element 67 which is preferably has a meniscus curved shape as illustrated. Astigmatic corrective lens element 67 serves to correct residual astigmatism which is encountered throughout the lens assembly shown in FIG. 10. Corrective lens element 67 transmits corrected divergent light 96 to a relay lens element group 97 which converges divergent light 96 to form light 98. Relay lens element group 97 preferably comprises lens components 68 and 69. Light 98 is transmitted to a second corrective lens element 90 which preferably has a meniscus curved shape which can be the same as or different from that of the first astigmatic corrective lens element 67, and which additionally corrects for astigmatism and other aberrations encountered throughout the lens assembly of FIG. 10. Corrective lens element 90 transmits additionally corrected light 99 to a field flattening lens group 100 which is very highly positively powered. Field flattening lens group 100 is preferably comprised of lens components 91, 92 and 93 arranged in series, and focuses light 99 onto flat imaging plane 13. Lens component 93 preferably has a very short focal length relative to flat image plane 13. The focal length of lens component 93 in this regard is preferably about 5 mm to about 100 mm; more preferably about 10 mm to about 50 mm; still more preferably about 20 mm. In another preferred practice of the lens assembly in FIG. 10, the lens elements and lens components as hereinbefore identified as forming said lens assembly are each bent sufficient to minimize residual aberrations and provide a high level of optical performance. In yet another preferred embodiment, optical filter 94 is interposed between flat imaging plane 13 and lens component last component of the field flattening lens element, shown in FIG. 10 as component 93. Preferably, an aperture stop is interposed between relay lens element 97 and the second astigmatic corrective lens 90; more preferably between component 69 and corrective lens 90. The lens assembly of FIG. 10 has a short working distance, i.e. the distance from the first astigmatic corrective lens element 67 and ophthalmic lens 22 is less than 30 mm.

In the lens assemblies illustrated in FIG. 6, 9 and 10, it is preferred that illuminating light 42, 56 and 95 is monochromatic wavelength in the range up to about 400 nm; preferably about 355 nm. It is also preferred but not mandatory that the lens elements and or their component lenses referred to in FIGS. 6, 9 and 10 are comprised of fused silica.

Figure 11:
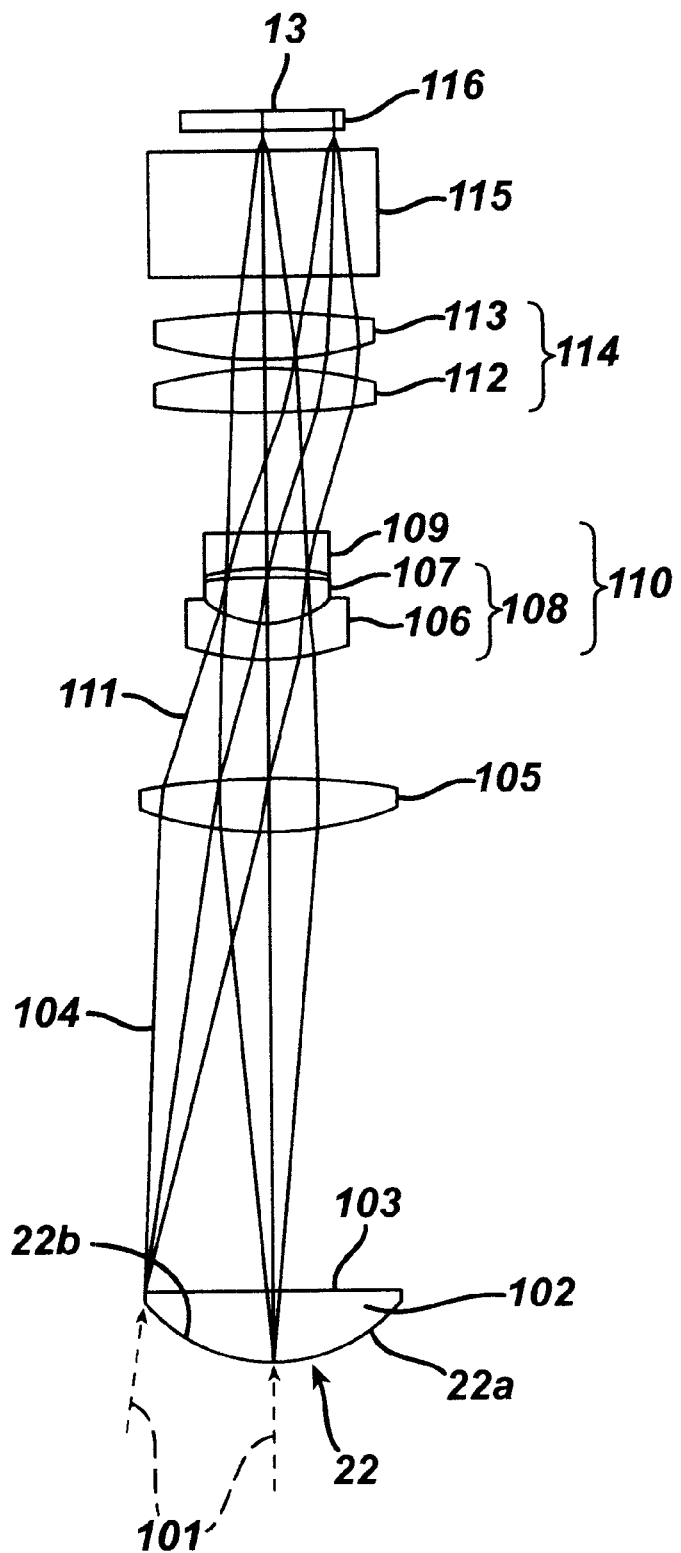
FIG. 11 is a diagram showing an embodiment of still yet another imaging lens assembly of the invention.

FIG. 11 illustrates an embodiment of an imaging lens assembly contemplated by the present invention to image an object having a steeply curved surface onto a flat imaging plane, where the curved surface is immersed in an aqueous fluid. Aqueous solutions in this regard include water and fluids having optical characteristics similar to water, such as saline solutions. This embodiment of the invention is especially useful for imaging an ophthalmic lens, such as a soft contact lens; when said lens is in its final packaging, typically translucent, which contains a saline solution in which said lens is immersed. In FIG. 11, ophthalmic lens 22 has a convex surface 22a and a concave surface 22b which is directed toward the lens assembly, the convex and concave surfaces 22a and 22b being as described in FIG. 6. Ophthalmic lens 22 is immersed in aqueous fluid 102, the surface 103 of said aqueous fluid being substantially flat, i.e. substantially ripple free. This includes practices wherein the final saline-containing packages are moving along a high speed conveyor using known techniques to maintain an adequately flat liquid level. Illuminating light 101 can, but need not, strike convex surface 22a at angles of incidence that are substantially normal over the entirety of surface 22a. As a practical matter in this regard, the translucent package acts as a diffuser, and by being in proximity to the ophthalmic lens within, significant amounts of light take the shortest path through ophthalmic lens 22. Light transmitted through ophthalmic lens 22 emerges from concave surface 22b as diverent light. A first refractive lens element 105 directs divergent light 104 to a relay lens group 110 which converges said light. Element 105 also preferably provides some minor function as a relay lens element and as a field lens element. Relay lens group 110 preferably comprises doublet 108 and relay lens component 109. Doublet 108 is preferably formed of a negative lens component cemented to a positive lens component where the positive lens component is of a material of construction that has a lower dispersion than the negative component. As exemplified in FIG. 11, doublet 108 is preferably comprised of a lens group formed from a concave lens component 106 having a negative power and a relatively high index value and a high dispersion value, cemented to positive power lens component 107 which has a lower index value and a lower dispersion value than component 106. Preferably, component 106 is comprised of SF14 glass or similar material; and component 107 is comprised of SK5 glass or some similar material. In FIG. 11, components 106 and 107 together provide the center element of the relay system of the lens assembly. Relay lens group 110 transmits light 111 to field flattening lens group 114 which focuses the light onto flat image plane 13. Field flattening lens group 114 preferably also functions as a refractive lens and serves to continue the relay function of 110 as well as provides a field lens function. In a preferred practice, filter 115 is interposed between flat image plane 13 and the field flattening lens element 114. It is further preferred that the sensor having the flat image plane 13 have a faceplate 116. As an example of materials of construction, without limitation to the invention, when 106 is SF14 and 107 is SK5 all other lens elements and/or their components can be SK5 with the exception of 115 and 116 which can be BK7 glass. In practice, the illuminating light 101 is at a wavelength that includes visible light; preferably illuminating light is at a wavelength of about 560 nm to about 640 nm. Given that the lens assembly of FIG. 11 performs in the visible spectrum, the lens assembly must be achromatic or color corrected so as to bring the wavelengths of interest to a common focus on image plane 13.

While the lens assemblies described hereinabove for FIGS. 6, 9, 10 and 11 all illustrate the steeply curved object being imaged as an ophthalmic lens, it will be appreciated by those of skill in the art that other steeply curved objects where the curve is concave and can be directed toward the lens assemblies are contemplated by the invention, and such objects can include spherical and aspherical objects.

Figure 12A:
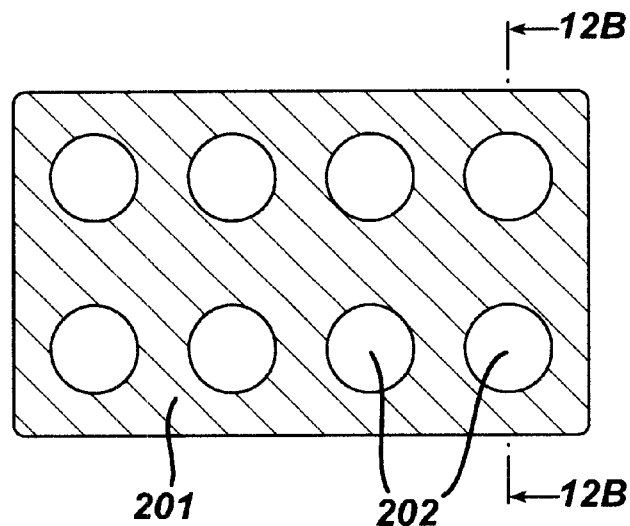
FIGS. 12A and 12B illustrate aspects of a lens carrier embodiment of the invention.
Figure 12B:
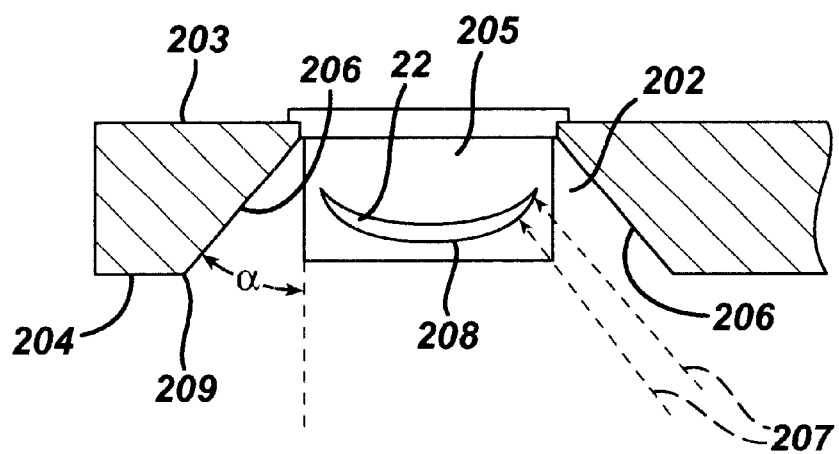

FIG. 12 illustrates an embodiment of a lens carrier contemplated by the invention. The carrier has especial utility in the practice of the invention wherein the light illuminating the ophthalmic lens being inspected impinges the convex surface of the lens facing the illumination at an angle of incidence that is nearly normal across the entire convex surface. In FIG. 12A, a lens carrier 201 is shown having a plurality of wells 202 extending therethrough. In practice, an ophthalmic lens is situated within container 205, e.g. the front curve mold part or the final packaging, which container is inserted into well 202. In FIG. 12B the carrier 201 is shown having a top surface 203 and a bottom surface 204, which bottom surface 204 faces the illuminating light during inspection. Ophthalmic lens 22 is situated such that its convex surface is situate the bottom of carrier 201 as shown in FIG. 12B. Well 202 of lens carrier 201 in cross section FIG. 12B is shown having a frustroconical shape, the diverging end 209 of which is located at the bottom surface 204. The sides 206 of the frustroconical well form angle α with the bottom surface 204. In a preferred practice, angle α is between about 35° to about 55°; more preferably, about 45°. At the angles indicated, illuminating light 207 is able to impinge lens 22 at angles that are substantially perpendicular to the convex surface 208 of lens 22. In another preferred practice, the sides of the well are treated to prevent reflections from sending light into ophthalmic lens 22 in a non-normal fashion. Without limitation in this regard, the sides 206 of the well can be bead blasted.

Figure 14:
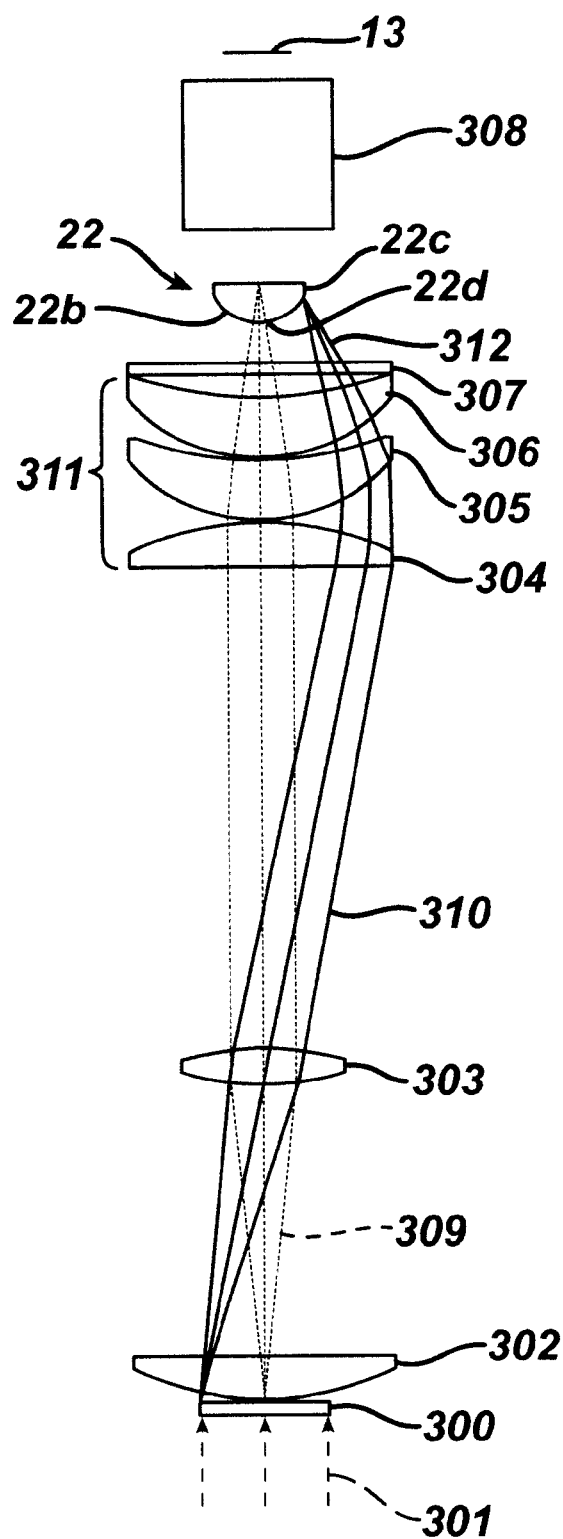
FIG. 14 is a diagram showing an embodiment of a lens assembly of the invention used to direct light onto a convex surface of an ophthalmic lens at nearly normal angles of incidence.

FIG. 14 illustrates an embodiment of a lens assembly of the present invention which can he used to direct light onto a convex surface such that the light strikes the surface at an angle of incidence substantially normal to same. In FIG. 14, collimated light 301 (as from a laser, e.g. EXCIMER 355 nm) which will be used to illuminate ophthalmic lens 22 having convex surface 22b, is incident on ground glass plate 300 which diffuses light 301 to an angle sufficient to illuminate ophthalmic lens 22. Diffuse light from diffuser 300 passes through a field lens element 302, which is preferably a planoconvex, lens, which takes the narrow cone of diffuse light from 300, converges and aims it (as light 309) at relay lens element 303. Relay lens element 303, which is preferably an equiconvex lens, at least partially collimates light 309 into substantially parallel beams 310 and directs these toward ophthalmic lens surface. 22b. Interposed between ophthalmic lens surface 22b and relay lens element 303 is focusing lens group 311 which is preferably comprised of a plurality of lens elements that converge and relay partially collimated light 310 to surface 22b as light 312. Light 312 strikes surface 22b at angles of incidence substantially normal to same. Thus light incident at the periphery 22c of ophthalmic lens 22 is nearly perpendicular to same, as is light incident at center 22d, as is light incident at points between 22d and 22c. Focusing lens group, 311 is preferably comprised of at least a planoconvex lens 304 and at least two meniscus lenses 305 and 306. Lenses 305 and 396 are preferably substantially identical. Focusing lens group 311 acts as a partial relay and partial field lens in directing the light to convex surface 22b. In a preferred practice, protective window 307 is placed aft of focusing lens group 311 to protect the elements thereof. In FIG. 14, light passing through ophthalmic lens 22 is transmitted to imaging lens assembly 308, which can be as depicted in FIGS. 6, 9 10 or 11, and then to imaging sensor 13.

EXAMPLE

The inspection of HEMA-based soft contact lenses for various cosmetic flaws and extraneous artifacts is compared. Representative of the practice of the present invention are the techniques identified hereinbelow as UV1 (typified by FIG. 1B) and UV2 (typified by FIG. 1C).

TABLE 1

| | | Techniques | | |
|---|---|---|---|---|
| | Bright Field | Dark Field | UV1 | UV2 |
| A Carrier imperfections | 2 | 4 | 1 | 1 |
| B Material Pulled up | 3 | 5 | 1 | 2 |
| C Missing material | 4 | 5 | 5 | 5 |
| D Deep voids | 3 | 5 | 5 | 5 |
| E Material torn | 1 | 3 | 1 | 2 |
| F Shallow voids | 1 | 4 | 2 | 4 |

In TABLE 1, the scale of 1–5 represents sensitivity. In descending order, the number 5 means that the technique will have the highest relative sensitivity to the subject artifact or flaw; the number 1 means the technique will have the least relative sensitivity to same. Of the artifacts, those identified as A and B, "carrier imperfections" and "material pulled up," represent extraneous artifacts that are unimportant to lens inspection. It is thus desirable that they have a sensitivity less (e.g. as close to 1 as possible) as opposed to cosmetic flaws C, D, E and F which are important to ophthalmic lens inspection and quality. As seen in TABLE 1, Bright Field (BF) and Dark Field (DF) will accord defects A and B sensitivity numbers greater than 1, meaning that these non-critical artifacts will be effectively undistinguishable from the important flaws C to F. Thus a pull (artifact B) will look like a cosmetic flaw under BF and DF, but since the thickness of the ophthalmic lens will not actually change thickness in this regard, the pull will be virtually invisible to UV1 and UV2 of the invention. Moreover, scratches in a lens carrier (artifact A) will look like flaws under BF and DF, but will produce a very low signal in UV1 and UV2 since again there will be no attendant change in lens thickness. Hence, unlike the prior art, the, invention is able to discriminate extraneous artifacts from true cosmetic flaws. In doing so, the invention enables a reduction in the number of false rejections and provides superior quality control.

What is claimed is:

1. A method for inspecting an ophthalmic lens which comprises:
   (a) illuminating an ophthalmic lens with light comprising a wavelength substantially absorptive to said lens;
   (b) detecting an image of at least part of said ophthalmic lens only from light that is at said substantially absorptive wavelength which has been transmitted through said ophthalmic lens; and
   (c) analyzing said image for changes in intensity of the light that is at said wavelength and that has been transmitted through said ophthalmic lens, said changes in intensity caused by changes in thickness of said ophthalmic lens.

2. The method of claim 1 wherein the changes in thickness of said ophthalmic lens are caused by cosmetic defects.

3. The method of claim 1 wherein the changes in thickness of said ophthalmic lens are designed into said lens.

4. The method of claim 3 wherein said changes in thickness designed into said lens are toric thin zones.

5. The method of claim 1 wherein said wavelength is at least 75% absorbed by said lens at the thickest part thereof.

6. The method of claim 5 wherein said wavelength is at least 85% absorbed by said lens at the thickest part thereof.

7. The method of claim 6 wherein said wavelength is at least 90% absorbed by said lens at the thickest part thereof.

8. The method of claim 7 wherein said wavelength is at least 95% absorbed by said lens at the thickest part thereof.

9. The method of claim 1 wherein said wavelength is up to about 400 nm.

10. The method of claim 9 wherein said wavelength is about 320 nm to about 355 nm.

11. The method of claim 1 wherein said wavelength is at least about 700 nm.

12. The method of claim 11 wherein said wavelength is about 700 nm to about 1000 nm.

13. The method of claim 1 wherein the light that illuminates said lens in step (a) consists essentially of said substantially absorptive wavelength.

14. The method of claim 13 wherein said light is obtained from a light source filtered to provide said substantially absorptive wavelength.

15. The method of claim 13 wherein said light is provided by a laser operating at said substantially absorptive wavelength.

16. The method of claim 1 wherein said ophthalmic lens is formed in a mold and the illuminating step (a) occurs while said lens is in at least part of said mold, said mold being substantially transparent to said wavelength.

17. The method of claim 1 wherein the illuminating step (a) occurs when said ophthalmic lens is in its final packaging.

18. The method of claim 1 wherein the ophthalmic lens has a convex surface and the light in step (a) illuminates the convex surface of said ophthalmic lens at an angle of incidence that is substantially normal to said convex surface.

19. The method of claim 1 wherein the ophthalmic lens has a concave surface and the light in step (a) illuminates the concave surface of said ophthalmic lens at an angle of incidence that is substantially normal to said concave surface.

20. The method of claim 1 wherein the ophthalmic lens has a concave surface and detecting step (b) employs an imaging lens assembly having a curved focal surface.

21. The method of claim 20 wherein said curved focal surface has a curvature substantially equal to the average curvature of the concave surface of the ophthalmic lens being illuminated.

22. A method for inspecting an ophthalmic lens which comprises:
   (a) providing light consisting essentially of one or more wavelengths up to about 400 nm;
   (b) illuminating with said light, an ophthalmic lens;
   (c) detecting, with light that has been transmitted through said ophthalmic lens, an image of at least part of said ophthalmic lens; and
   (d) analyzing said image for changes in intensity of the light that has been transmitted through said ophthalmic lens, said changes in intensity caused by changes in thickness of said ophthalmic lens.

23. The method of claim 22 wherein said changes in thickness are caused by cosmetic flaws.

24. The method of claim 22 wherein said changes in thickness are designed into said ophthalmic lens.

25. The method of claim 24 wherein said changes in thickness designed into the ophthalmic lens are toric thin zones.

26. The method of claim 22 wherein the light of step (a) is from a light source that has been filtered sufficient to provide light at said wavelength.

27. The method of claim 26 wherein said light is at a wavelength of about 280 nm to about 360 nm.

28. A method for inspecting an ophthalmic lens which comprises:
   (a) providing light from a laser operating at a wavelength up to about 400 nm;
   (b) illuminating, with said light, an ophthalmic lens;
   (c) detecting, with light that has been transmitted through said ophthalmic lens, an image of at least part of said lens; and
   (d) analyzing said image for changes in intensity of the light that has been transmitted through said ophthalmic lens, said changes in intensity caused by changes in thickness of said ophthalmic lens.

29. The method of claim 28 wherein said changes in thickness are caused by cosmetic flaws.

30. The method of claim 28 wherein said changes in thickness are designed into said ophthalmic lens.

31. The method of claim 30 wherein said changes in thickness designed into said ophthalmic lens are toric thin zones.

32. The method of claim 28 wherein said wavelength is about 355 nm.

33. The method of claim 28 wherein said ophthalmic lens has a convex surface said convex surface being illuminated in illuminating step (b), said light in step (b) illuminating said convex surface at an angle of incidence that is substantially normal over the entirety of said convex surface.

34. The method, of claim 28 wherein said ophthalmic lens has a concave surface, said concave surface being illuminated in illuminating step (b), said light in step (b) illuminating said concave surface at an angle of incidence that is substantially normal over the entirety of said concave surface.

35. A system for inspecting an ophthalmic lens which comprises:
   (a) an illumination subsystem to generate light and to direct said light through an ophthalmic lens at an inspection position, said light comprising a wavelength substantially absorptive to said ophthalmic lens;
   (b) an imaging subsystem to detect an image of at least part of said ophthalmic lens from only light that is at said wavelength which has been transmitted through said ophthalmic lens; and
   (c) an image processing subsystem to analyze said image for changes in intensity of the light that is at said wavelength and that has been transmitted through said ophthalmic lens, said changes in intensity caused by changes in thickness of said ophthalmic lens.

36. The method of claim 35 wherein the changes in thickness are caused by cosmetic flaws.

37. The method of claim 35 wherein the changes in thickness are designed into said ophthalmic lens.

38. The method of claim 37 wherein said changes in thickness designed into said lens are toric thin zones.

39. The system of claim 35 wherein said illumination subsystem (a) comprises a light source that is filtered to provide light consisting essentially of said wavelength prior to directing said light, through said ophthalmic lens.

40. The system of claim 35 wherein said imaging subsystem (b) comprises a camera having a spectral response to said wavelength and an imaging lens assembly that transmits said wavelength.

41. The system of claim 35 further comprising a filtering subsystem located after said inspection position to filter light that has been directed through said ophthalmic lens to light consisting essentially of said wavelength.

42. The system of claim 35 wherein said illumination subsystem (a) comprises a laser light source providing a laser light beam at said wavelength.

43. The system of claim 42 wherein said illumination subsystem further comprises a beam expander component and an apodizing component located in the path of said laser light beam.

44. The system of claim 43 wherein said apodizer produces a bull's eye pattern from said laser light beam.

45. The system of claim 44 wherein said apodizer has a central area, a middle area, and a peripheral area, and wherein said middle area has an optical density to said laser light about 10 times greater than the optical density of said central area, and wherein said peripheral area has an optical density to said laser light about 10 times greater than that for the middle area.

46. The system of claim 45 wherein said apodizer further comprises an annular area interposed between said central area and said middle area, said annular area having an optical density about 10 times less that said central area.

47. The system of claim 44 wherein said apodizer is comprised of a diffractive holographic element.

* * * * *